(12) United States Patent
Berelsman et al.

(10) Patent No.: US 8,585,768 B2
(45) Date of Patent: Nov. 19, 2013

(54) ELBOW PROSTHESIS

(75) Inventors: Brian K Berelsman, Warsaw, IN (US); Kevin T Stone, Winona Lake, IN (US); Russell M Parrott, Winona Lake, IN (US); Hill Hastings, Zionsville, IN (US); Thomas J Graham, Lutherville, MD (US)

(73) Assignee: Biomet Manufacturing, LLC, Warsaw, IN (US)

( * ) Notice: Subject to any disclaimer, the term of this patent is extended or adjusted under 35 U.S.C. 154(b) by 1065 days.

(21) Appl. No.: 11/384,943

(22) Filed: Mar. 17, 2006

(65) Prior Publication Data

US 2006/0173546 A1 Aug. 3, 2006

Related U.S. Application Data

(63) Continuation-in-part of application No. 10/333,140, filed as application No. PCT/US01/22338 on Jul. 17, 2001, now Pat. No. 7,247,170.

(60) Provisional application No. 60/219,103, filed on Jul. 18, 2000.

(51) Int. Cl.
*A61F 2/38* (2006.01)

(52) U.S. Cl.
USPC .............. 623/20.12; 623/20.11; 623/20.13

(58) Field of Classification Search
USPC ........................... 623/20.11–20.13
See application file for complete search history.

(56) References Cited

U.S. PATENT DOCUMENTS

| | | |
|---|---|---|
| 3,547,115 A | 12/1970 | Stevens |
| 3,694,821 A | 10/1972 | Moritz |
| 3,708,805 A | 1/1973 | Scales et al. |
| 3,816,854 A | 6/1974 | Schlein |
| 3,824,630 A | 7/1974 | Johnston |
| 3,852,831 A | 12/1974 | Dee |
| 3,919,725 A | 11/1975 | Swanson et al. |
| 3,939,496 A | 2/1976 | Ling et al. |
| 3,946,445 A | 3/1976 | Bentley et al. |
| 3,990,117 A | 11/1976 | Pritchard et al. |
| 3,991,425 A | 11/1976 | Martin et al. |

(Continued)

FOREIGN PATENT DOCUMENTS

| | | |
|---|---|---|
| DE | 28 06 717 | 2/1978 |
| DE | 3417923 A1 | 11/1985 |

(Continued)

OTHER PUBLICATIONS

Latitude®, "Total Elbow Prosthesis, A new generation is born naturally precise", TORNIER [undated].

(Continued)

*Primary Examiner* — David Isabella
*Assistant Examiner* — Joshua Levine
(74) *Attorney, Agent, or Firm* — Harness, Dickey

(57) ABSTRACT

A method and apparatus for replacing a selected portion of the anatomy is described. In particular, a prosthesis can be provided to replace a portion of an articulating joint, such as an elbow. The apparatus can be modular for various reasons and each of the modular portions can include a different dimension to achieve a selected result. For example, the prosthesis can achieve a different size condylar replacement, a selected offset, a selected articulation, or combinations thereof.

15 Claims, 21 Drawing Sheets

(56) References Cited

U.S. PATENT DOCUMENTS

| | | | |
|---|---|---|---|
| 4,001,603 | A | 1/1977 | Wilcox |
| 4,008,495 | A | 2/1977 | Cavendish et al. |
| 4,038,704 | A | 8/1977 | Ring |
| 4,079,469 | A | 3/1978 | Wadsworth |
| 4,129,902 | A | 12/1978 | Harmon |
| 4,131,956 | A | 1/1979 | Treace |
| 4,131,957 | A | 1/1979 | Bokros |
| 4,194,250 | A | 3/1980 | Walker |
| 4,206,516 | A | 6/1980 | Pilliar |
| 4,224,695 | A | 9/1980 | Grundei et al. |
| 4,224,697 | A | 9/1980 | Murray et al. |
| 4,242,758 | A | 1/1981 | Amis et al. |
| 4,259,752 | A | 4/1981 | Taleisnik |
| 4,280,231 | A | 7/1981 | Swanson |
| 4,293,963 | A | 10/1981 | Gold et al. |
| 4,301,552 | A | 11/1981 | London |
| 4,352,212 | A | 10/1982 | Greene et al. |
| 4,378,607 | A | 4/1983 | Wadsworth |
| 4,383,337 | A | 5/1983 | Volz et al. |
| 4,479,271 | A | 10/1984 | Bolesky et al. |
| 4,538,306 | A | 9/1985 | Dörre et al. |
| 4,659,331 | A | 4/1987 | Matthews et al. |
| 4,725,280 | A | 2/1988 | Laure |
| 4,759,768 | A | 7/1988 | Hermann et al. |
| 4,822,364 | A | 4/1989 | Inglis et al. |
| 4,911,719 | A | 3/1990 | Merle |
| 4,927,422 | A | 5/1990 | Engelhardt |
| 4,936,853 | A | 6/1990 | Fabian et al. |
| 5,024,670 | A | 6/1991 | Smith et al. |
| 5,030,237 | A | 7/1991 | Sorbie et al. |
| 5,207,711 | A | 5/1993 | Caspari et al. |
| 5,282,867 | A | 2/1994 | Mikhail |
| 5,314,484 | A * | 5/1994 | Huene ................ 623/20.12 |
| 5,376,121 | A * | 12/1994 | Huene et al. ............ 623/20.12 |
| 5,380,334 | A | 1/1995 | Torrie et al. |
| 5,411,555 | A | 5/1995 | Nieder |
| 5,507,821 | A | 4/1996 | Sennwald et al. |
| 5,507,826 | A | 4/1996 | Besselink et al. |
| 5,549,685 | A * | 8/1996 | Hayes ................ 623/20.16 |
| 5,584,835 | A | 12/1996 | Greenfield |
| 5,665,087 | A | 9/1997 | Huebner |
| 5,702,471 | A | 12/1997 | Grundei et al. |
| 5,725,541 | A | 3/1998 | Anspach, III et al. |
| 5,725,591 | A | 3/1998 | DeCarlo, Jr. et al. |
| 5,782,923 | A | 7/1998 | Engelbrecht et al. |
| 5,840,078 | A | 11/1998 | Yerys |
| 5,879,395 | A | 3/1999 | Tornier et al. |
| 5,980,557 | A | 11/1999 | Iserin et al. |
| 6,027,534 | A | 2/2000 | Wack et al. |
| 6,120,543 | A | 9/2000 | Kubein-Meesenburg et al. |
| 6,162,253 | A | 12/2000 | Conzemius et al. |
| 6,290,725 | B1 | 9/2001 | Weiss et al. |
| 6,306,171 | B1 | 10/2001 | Conzemius |
| 6,379,387 | B1 | 4/2002 | Tornier |
| 6,626,906 | B1 | 9/2003 | Young |
| 6,656,225 | B2 | 12/2003 | Martin |
| 6,699,290 | B1 | 3/2004 | Wack et al. |
| 6,767,368 | B2 * | 7/2004 | Tornier ................ 623/20.12 |
| 6,814,757 | B2 | 11/2004 | Kopylov et al. |
| 6,890,357 | B2 | 5/2005 | Tornier |
| 7,247,170 | B2 | 7/2007 | Graham et al. |
| 7,527,650 | B2 * | 5/2009 | Johnson et al. ............ 623/20.14 |
| 2002/0165614 | A1 | 11/2002 | Tornier |
| 2004/0186580 | A1 | 9/2004 | Steinmann |
| 2004/0243243 | A1 | 12/2004 | Tornier |
| 2004/0254574 | A1 | 12/2004 | Morrison et al. |
| 2005/0216090 | A1 | 9/2005 | O'Driscoll et al. |
| 2006/0173546 | A1 | 8/2006 | Berelsman et al. |
| 2006/0247786 | A1 | 11/2006 | Ball |
| 2008/0015706 | A1 | 1/2008 | Berelsman et al. |
| 2008/0033566 | A1 | 2/2008 | Berelsman et al. |
| 2008/0154384 | A1 | 6/2008 | Acker et al. |
| 2008/0183291 | A1 | 7/2008 | Scheller et al. |
| 2008/0188942 | A1 | 8/2008 | Brown et al. |
| 2009/0105839 | A1 | 4/2009 | Ikegami et al. |
| 2010/0087928 | A1 | 4/2010 | Graham et al. |
| 2010/0179661 | A1 | 7/2010 | Berelsman et al. |
| 2010/0222887 | A1 | 9/2010 | Katrana et al. |

FOREIGN PATENT DOCUMENTS

| | | |
|---|---|---|
| EP | 1051954 A1 | 11/2000 |
| EP | 1481653 A1 | 12/2004 |
| FR | 2419718 A1 | 10/1979 |
| FR | 2 634 373 | 1/1990 |
| GB | 1 520 162 | 8/1978 |
| SU | 1560-183 A | 7/1988 |
| SU | 1567-200 A | 5/1990 |

OTHER PUBLICATIONS

Discovery Elbow System brochure, Surgical Technique, Biomet Orthopedics, Inc., © 2002.

Joint Replacement, Overview, © DePuy Orthopaedics, Inc., www.jointreplacement.com/xq/ASP.default/mn.local/pg.list/joint_id.2/list_id.59/newFont.2/joint_nm.Elbow/local_id.18/qx/default.htm, 2000-2004.

Joint Replacement, Surgery, © DePuy Orthopaedics, Inc., www.jointreplacement.com/xq/ASP.default/mn.local/pg.list/joint_id.2/list_id.59/newFont.2/joint_nm.Elbow/local_id.18/qx/default.htm, 2000-2004.

DePuy Orthopaedics, Inc., web page print out—http://www/allaboutarthritis.com/AllAboutArthritis/layoutTemplates/html/en/contentdisplay/document/condition/arthritis/clinicalArticle/Elbow_Replacement_Surgery.htm, 2000-2005—printed Dec. 14, 2005.

Sorbie-Questor® Total Elbow System, Extremities (2003) Wright Medical Technology, Inc., 1 page.

International Search Report and Written Opinion for PCT/US2010/049314 mailed Feb. 21, 2011.

International Search Report and Written Opinion for PCT/US2009/057449 mailed Feb. 21, 2011.

International Preliminary Report on Patentability and Written Opinion for PCT/US2009/057449 Mailed Sep. 9, 2011.

Latitude®, "Total Elbow Prosthesis, Surgical Technique", TORNIER pp. 1-39 [undated].

Non-Final Office Action for U.S. Appl. No. 12/391,904, mailed Nov. 1, 2012.

Non-Final Office Action regarding U.S. Appl. No. 12/780,424, mailed Nov. 2, 2012.

Non-Final Office Action regarding U.S. Appl. No. 12/562,616, mailed May 17, 2012.

* cited by examiner

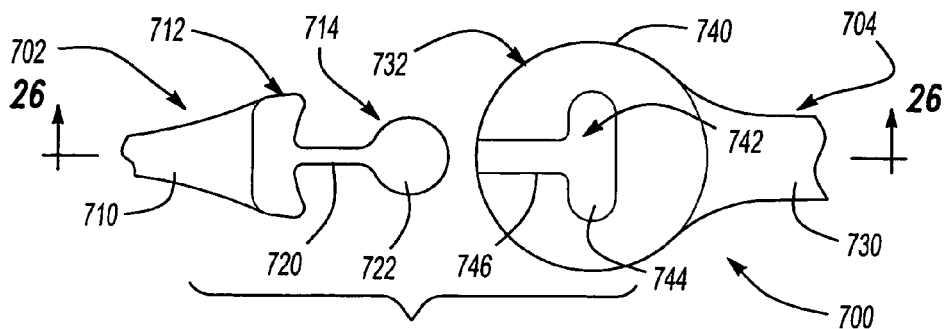
_Fig-25_
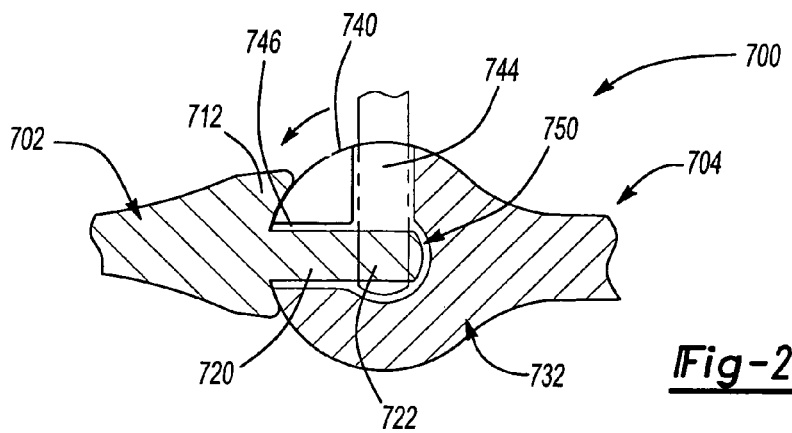
_Fig-26_
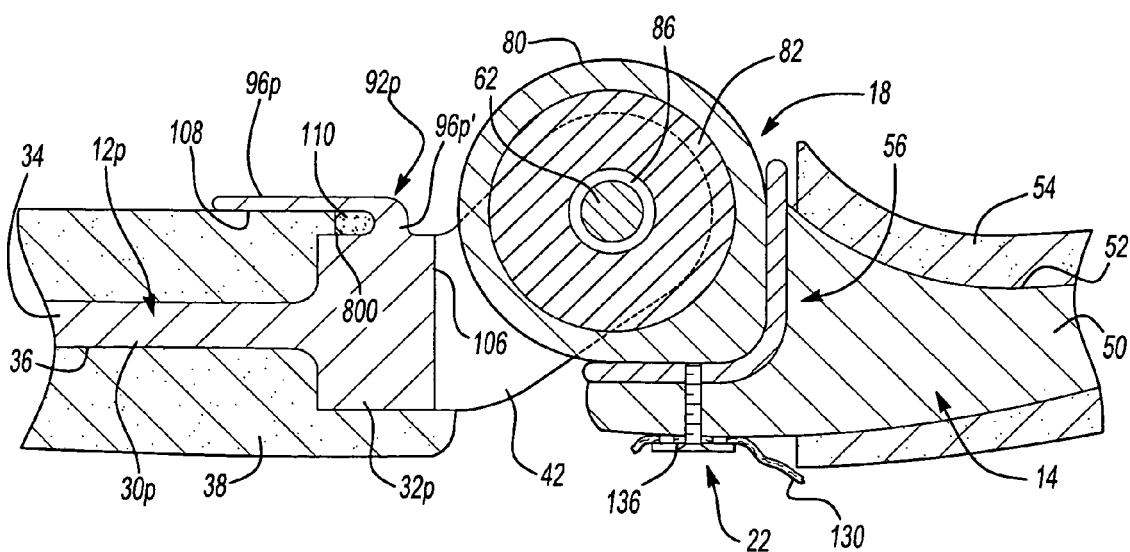
_Fig-27_

ELBOW PROSTHESIS

CROSS-REFERENCE TO RELATED APPLICATIONS

This application is a continuation-in-part of U.S. patent application Ser. No. 10/333,140 filed on Jan. 15, 2003, which is a National Stage of International Application No. PCT/US01/22338 (published as WO 02/05728), filed Jul. 17, 2001, which claims priority to U.S. Provisional Application No. 60/219,103 filed Jul. 18, 2000. Each of these disclosures are incorporated herein by reference.

FIELD

The present teachings relate generally to prosthetic devices used in arthroplasty and more particularly to a modular elbow prosthesis.

BACKGROUND

The present teachings relate generally to prosthetic devices used in arthroplasty and more particularly to a modular elbow prosthesis.

Linked or constrained elbow prostheses are known which comprise simple hinge arrangements, one component of which is attached to the end of the humerus and the other component of which is attached to the end of the ulna. The humeral component includes a shaft, that is cemented into a prepared cavity in the end of the humerus, and the ulnar component includes a shaft, that is cemented to the end of the ulna. The components of the prosthesis are connected together by means of a hinge pin so that the prosthesis allows a single degree of freedom of movement of the ulna relative to the humerus.

One example of a linked elbow prostheses is disclosed in U.S. Pat. No. 6,027,534 to Wack et al. In several respects, the linked embodiment of the '534 patent is typical of the designs for linked elbow prostheses in that it includes a humeral stem that terminates at a yoke at its distal end, a bearing component, a retaining pin and an ulna stem. The bearing component includes an oversized hole that is aligned with the longitudinal axis of the bearing and adapted to accept the retaining pin in a slip-fit condition. The distal end of the bearing component is coupled to the ulna stem. Despite the relatively widespread use of designs of this type, several drawbacks have been noted.

One significant drawback concerns the assembly of the elbow prosthesis after the surgeon has cemented the humeral and ulna stems to their respective bones. In using such conventionally configured linked elbow prosthesis devices, it is frequently necessary for the surgeon to drill a fairly large hole through the humerus so that the retaining pin may be inserted to the yoke of the humeral stem and the humeral bearing component. As a high degree of accuracy is typically required to ensure proper alignment between the hole in the humerus and the hole in the yoke of the humeral stem, a significant cost can be associated with this step in the installation of an elbow prosthesis due to the cost of the tooling used and the amount of time required to complete this step. The other method for attaching the prosthetic device includes inserting the device in its linked condition or placing the remaining piece into the yoke prior to fully seating the humeral component into the bone. This later method is typically somewhat difficult, given the limited amount of joint space that is available and the time constraints associated with the use of a PMMA bone cement.

Unlinked, or unconstrained, elbow prostheses are known which are similar to linked elbow prostheses but do not have a specific component which mechanically couples the humeral and ulnar stems together. Rather, the prosthetic device is held together by the patient's natural soft tissues. One example of an unlinked elbow prostheses is also disclosed in U.S. Pat. No. 6,027,534 to Wack et al. In several respects, the unlinked embodiment of the '534 patent is similar to the linked embodiment discussed above in that it includes a humeral stem that terminates at a yoke at its distal end, a humeral bearing component, a retaining pin, an ulnar bearing component and a ulnar stem. The outer surface of the humeral bearing is contoured to match the contour of the ulnar bearing component. Despite the relatively widespread use of designs of this type, several drawbacks have been noted.

For instance, a retaining pin that is transverse to the longitudinal axis of the patient is employed, thereby making its removal difficult if a bearing need to be replaced.

SUMMARY

It is taught to provide a prosthetic joint kit which transmits load through mating bearing components over a spherically shaped area so as to minimize stresses in the bearing components, more accurately mimic normal joint motion and provide for ease of assembly and revision.

In various forms, the teachings provide a prosthetic joint kit having a first bearing component and a second bearing component. The first bearing component includes a pair of condyle portions, each of which having a spherically shaped bearing portion. The second bearing component includes a pair of spherical bearing portions which are configured to engage the spherically shaped bearing portions of the first bearing component.

It is also taught to provide a prosthetic joint kit having a high degree of modularity to permit a surgeon to easily configure the prosthetic joint kit to a patient.

It is also taught to provide a prosthetic joint kit having a plurality of modular and interchangeable joint components which permit a surgeon to easily configure the prosthetic joint kit to a patient. Modularity is achieved through a plurality of interchangeable components such as stem structures, bearing components and bearing inserts.

According to various embodiments it is taught to provide a prosthetic joint kit having a plurality of interchangeable bearing inserts which permit a surgeon to tailor the degree of varus/valgus constraint in a desired manner.

According to various embodiments it is taught to provide a prosthetic joint kit having a plurality of interchangeable bearing inserts, each of which having a pair of spherical depressions. Each of the spherical depressions has a first portion and a second portion, with the second portion being formed in a manner that defines the degree of varus/valgus constraint.

According to various embodiments it is taught to provide a prosthetic joint kit which effectively limits the amount by which the prosthetic joint will articulate.

According to various embodiments it is taught to provide a prosthetic joint kit having a cam structure which is coupled to a first stem structure such that the first stem structure contacts a second stem when the first stem structure has been rotated to a predetermined position relative to the second stem structure.

According to various embodiments it is taught to provide a prosthetic joint kit which employs a spherically-shaped bearing surface to transmit load between stem structures yet does not require fasteners or other hardware to link the stem structures together.

According to various embodiments it is taught to provide a prosthetic joint kit having a first stem structure with a retaining structure and a first spherical bearing surface and a second stem structure with a retaining aperture and a second spherical bearing surface. The retaining aperture is configured to receive the retaining structure when the first stem structure is at a first orientation relative to the second stem structure. Relative rotation of the first stem structure from the first orientation causes retaining structure to engage a portion of the retaining aperture which precludes the withdrawal of the retaining structure therefrom. The retaining aperture and retaining structure are sized so as not to transmit load therebetween, thereby ensuring that load is transmitted between the spherical bearing surfaces of the first and second stem structures.

Further areas of applicability will become apparent from the description provided herein. It should be understood that the description and specific examples are intended for purposes of illustration only and are not intended to limit the scope of the present disclosure.

DRAWINGS

Additional advantages and features of the present teachings will become apparent from the subsequent description and the appended claims, taken in conjunction with the accompanying drawings, wherein:

FIG. 25 is an exploded top plan view of a linked prosthetic joint kit constructed in accordance with the teachings of a various embodiment of a fifth aspect of the present teachings;

FIG. 26 is a longitudinal cross-sectional view of the linked prosthetic joint kit of FIG. 25;

FIG. 27 is a longitudinal cross-sectional view similar to that of FIG. 2, but illustrating the stem with an integrally-formed flange for compressing a bone graft;

DETAILED DESCRIPTION OF VARIOUS EMBODIMENTS

Figure 1:
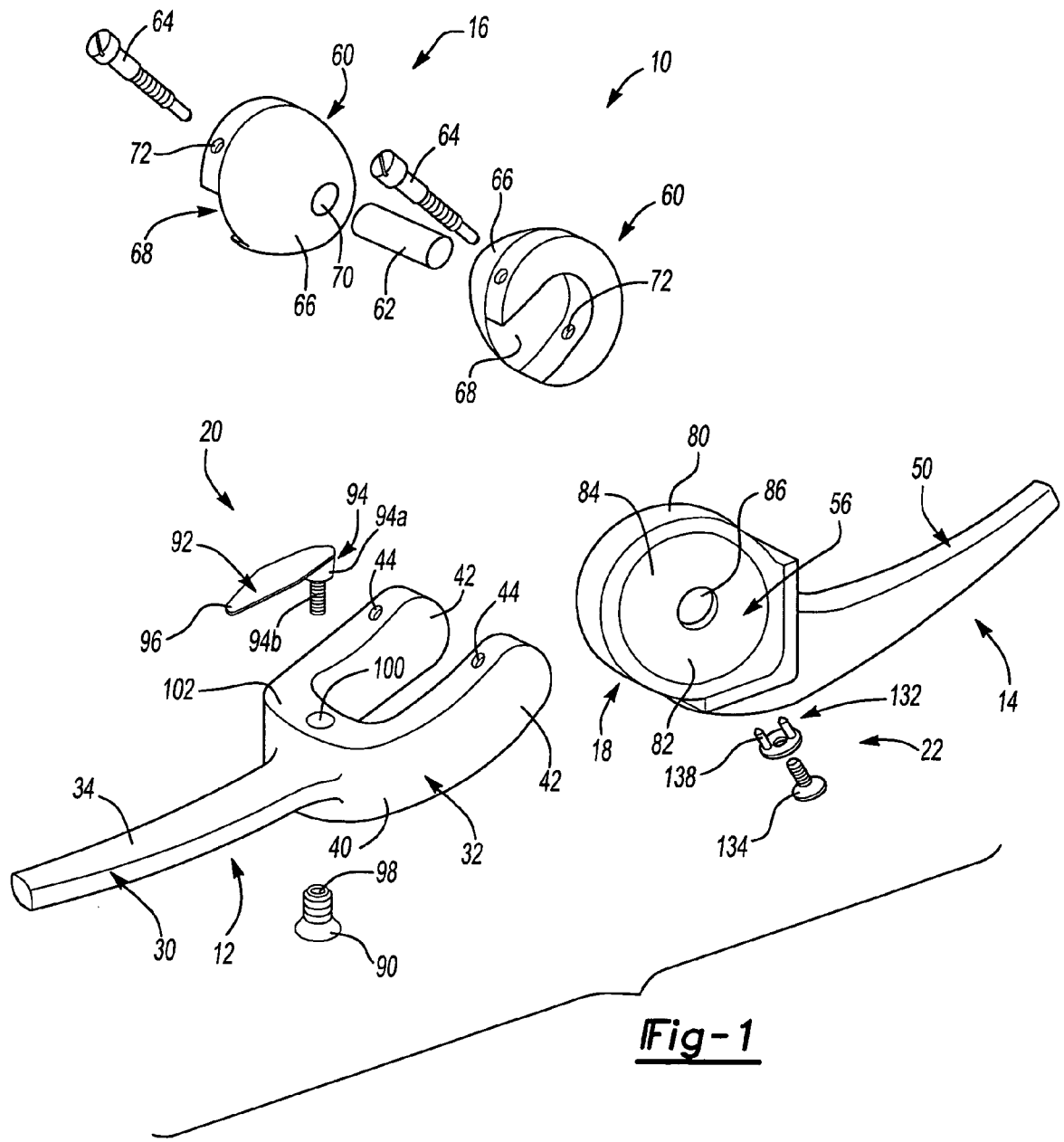
FIG. 1 is an exploded perspective view of a linked prosthetic joint kit constructed in accordance with the teachings of a first aspect of the present teachings.

The following description is merely exemplary in nature and is not intended to limit the present disclosure, application, or uses. It should be understood that throughout the drawings, corresponding reference numerals indicate like or corresponding parts and features.

Figure 2:
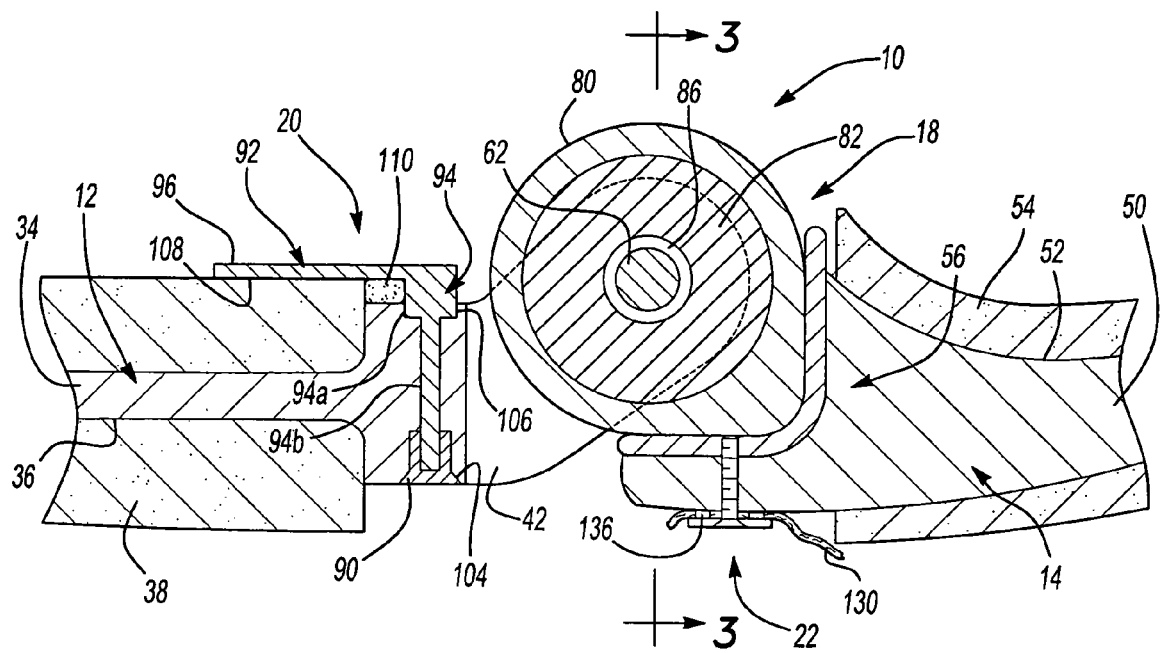
FIG. 2 is a longitudinal cross-sectional view of the linked prosthetic joint kit of FIG. 1 implanted in the arm of a person.
Figure 3:
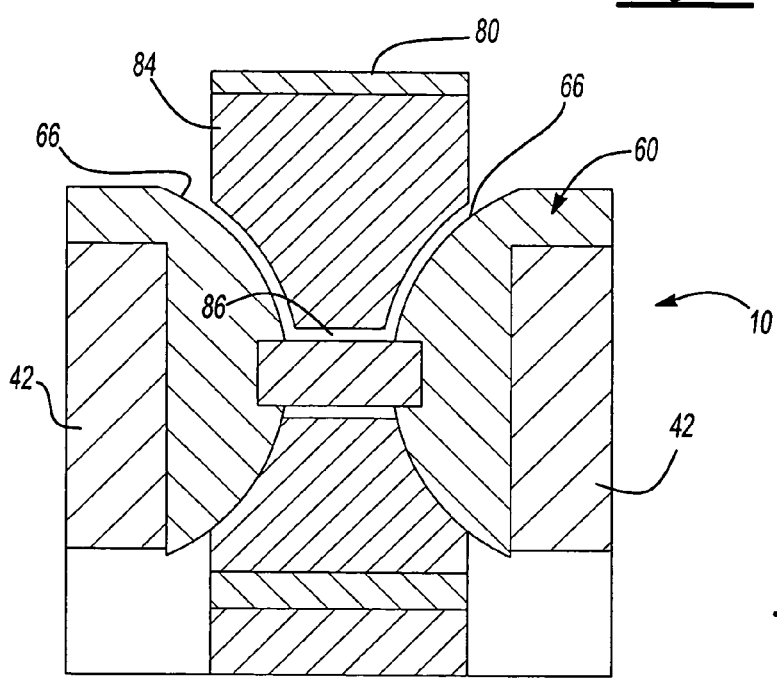
FIG. 3 is a cross-sectional view taken along the line 3-3 of FIG. 2.

With reference to FIGS. 1, 2 and 3 of the drawings, a linked prosthetic joint device constructed in accordance with the teachings of a first aspect is generally indicated by reference number 10. Although the particular prosthesis illustrated and discussed relates to a prosthesis for use in reconstructing an elbow, it will be understood that the teachings have applicability to other types of linked and unlinked prosthetic devices. As such, the scope of the present teachings will not be limited to applications involving elbow prosthesis but will extend to other prosthetic applications.

In the particular embodiment illustrated, linked prosthetic joint 10 is shown to include a first stem structure 12, a second stem structure 14, a first bearing component 16, a second bearing component 18, a modular flange 20 and a tissue fastener 22. First stem structure 12 includes a proximal portion 30 and a distal portion 32. Proximal portion 30 includes a stem member 34 which is adapted to fit within the medullary canal 36 of a humerus 38. Distal portion 32 includes a generally U-shaped member 40 which is fixedly coupled to the distal end of proximal portion 30. U-shaped portion 40 includes a pair of spaced-apart legs or furcations 42. A threaded fastener aperture 44 extends perpendicularly through each of the furcations 42.

Second stem structure 14 includes a distal portion 50 which is adapted to fit within the medullary canal 52 of an ulna 54. Second stem structure 14 also includes a proximal portion 56 which is coupled to second bearing component 18. In the particular embodiment illustrated, second bearing component 18 is fixedly coupled to second stem structure 14. However, second bearing component 18 may also be releasably coupled to second stem structure 14 as shown in FIGS. 9 through 12.

First bearing component 16 includes a pair of condyle portions 60, a pin portion 62 and a pair of fasteners 64. Condyle portions 60 and pin portion 62 are formed from a suitable material, such as cobalt chromium alloy. Each condyle portion 60 is shown to include a spherically-shaped bearing portion 66, slotted aperture 68, a pin aperture 70 and a mounting aperture 72. The pair of spherically shaped bearing portions 66 collectively form a first bearing surface. Pin aperture 70 is sized to receive an end of pin portion 62 to permit pin portion 62 to slidingly engage condyle portions 60. Pin 62 can also be fixedly coupled with one of said condyle portion 60 and slidingly engage second of said condyle portion 60. Each of the slotted apertures 68 is sized to slidingly engage one of the furcations 42.

Second bearing component 18 is shown to include a cage portion 80 which is fixedly coupled to the proximal portion 56 of second stem structure 14 and a bearing member 82 which is fixedly coupled to the cage portion 80. Bearing member 82 includes a pair of spherical bearing portions 84 which are configured to engage the spherically shaped bearing portions 66 of the condyle portions 60. The pair of spherical bearing surfaces 84 collectively form a second bearing surface that mates with the first bearing surface. Bearing member 82 also includes a through hole 86 which is adapted to receive pin portion 62, preferably without transmitting load therebetween (i.e., pin portion 62 preferably does not contact the surfaces of through hole 86). In the particular embodiment illustrated, bearing member 82 is fabricated from polyethylene which has been molded to cage portion 80. Alternatively, bearing member 82 may be fabricated from any other appropriate material such as a stainless steel, ceramic, pyrolytic carbon, cobalt chrome (CoCr) etc.

To use linked prosthetic joint 10, first stem structure 12 is implanted in humerus 38 such that proximal portion 34 is located in the medullary canal 36 of the humerus 38 as shown in FIG. 2. Second stem structure 14 is similarly implanted in ulna 54 such that distal portion 50 is located in the medullary canal 52. Pin portion 62 is next inserted to the pin aperture 70 of one of the condyle portions 60 and the opposite end of pin portion 62 is placed through hole 86 and into the pin aperture 70 of the other one of the condyle portions 60. Second bearing component 18 is positioned adjacent the distal portion 32 of first stem structure 12, furcations 42 are aligned to their respective slotted aperture 68 and condyle portions 60 are slidingly engaged to furcations 42. Fasteners 64 are inserted through their respective mounting apertures 72 and threadably engaged to their threaded fastener aperture 44. When fully seated, each of the fasteners 72, extends through its respective furcation 42 to prevent condyle portion 60 from rotating relative to the furcation 42. At this point, first and second bearing components 16 and 18 hingedly couple first and second stem structures 12 and 14 together in a linked or constrained manner.

Construction of linked prosthetic joint 10 in this manner is highly advantageous in that it permits the surgeon to insert the first and second stem structures 12 and 14 prior to or after assembling linked prosthetic joint 10, as well as permits linked prosthetic joint 10 to be assembled in a relatively small space as compared to most of the other prosthetic joints that are known in the art. Furthermore, the spherical configuration of first and second bearing surfaces 66 and 84 permits the load which is transmitted through linked prosthetic joint 10 to be spread out over a relatively large area, rather than concentrated at a single point or over a line of contact to thereby improve the durability of linked prosthetic joint 10.

Modular flange 20 may be employed to increase the resistance of first stem structure 12 to rotation within medullary canal 36. In FIGS. 1 and 2, modular flange 20 is shown to include an internally threaded fastener 90, and a unitarily formed flange structure 92 having a mount member 94 and a flange member 96. Mount member 94 includes a locating cylinder 94a which is fixedly coupled to flange member 96 at its base and an externally threaded fastener 94b which is coupled to an opposite side of locating cylinder 94a. A mounting hole 98, which is sized to receive fastener 94b, extends through internally threaded fastener 90. A bore 100 formed through the base 102 of U-shaped portion 40 has a first portion 104 which is tapered at one end to engage the edges of internally threaded fastener 90 and second portion 106 which is counter bored at the other end to engage the locating cylinder 94a of mount member 94. Internally threaded fastener 90 is threadably engaged to fastener 94b to fixedly but removably couple modular flange 20 to first stem structure 12.

Modular flange 20 may be employed to generate a clamping force which clamps a portion 108 of the humerus 38 between the proximal portion 34 of the first stem structure 12 and the flange member 96. Preferably, a bone graft 110 is employed in conjunction with modular flange 20 such that the clamping force produced by modular flange 20 is also transmitted to bone graft 110 to promote the attachment of bone graft 110 to humerus 38 and the subsequent growth of bone graft 110. Those skilled in the art will understand that alternatively, a flange (not shown) which is unitarily formed with first stem structure 12 may be incorporated into linked prosthetic joint 10 to thereby increase the resistance of first stem structure 12 to rotation within medullary canal 36. However, a flange which is unitarily formed with first stem structure 12 could not be employed to generate a clamping force which clamps a portion 108 of the humerus 38 between the proximal portion 34 of the first stem structure 12 and the flange.

Tissue fastener 22 is shown in FIGS. 1 and 2 to be a device for attaching soft tissue, such as tendons 130, to linked prosthetic joint 10. In this regard, the specific configuration of tissue fastener is beyond the scope of this disclosure. Examples of suitable tissue fasteners are discussed in U.S. Pat. Nos. 5,380,334, 5,584,835, 5,725,541, 5,840,078 and 5,980,557 which are hereby incorporated by reference as if fully set forth herein.

In the particular embodiment illustrated, tissue fastener 22 is shown to include a tissue clamp 132 and a threaded fastener 134. Tissue clamp 132 includes an annular base 136 and a pair of prongs 138. Prongs 138 are forced through the soft tissue (e.g. tendons 130). Threaded fastener 134 is inserted through a hole in base 136 and threadably engaged to second stem structure 14, to fixedly but releasably couple tissue fastener 22 and the soft tissue to second stem structure 14. Those skilled in the art will understand that tissue fastener 22 may also be used in conjunction with first stem structure 12.

Figure 1A:
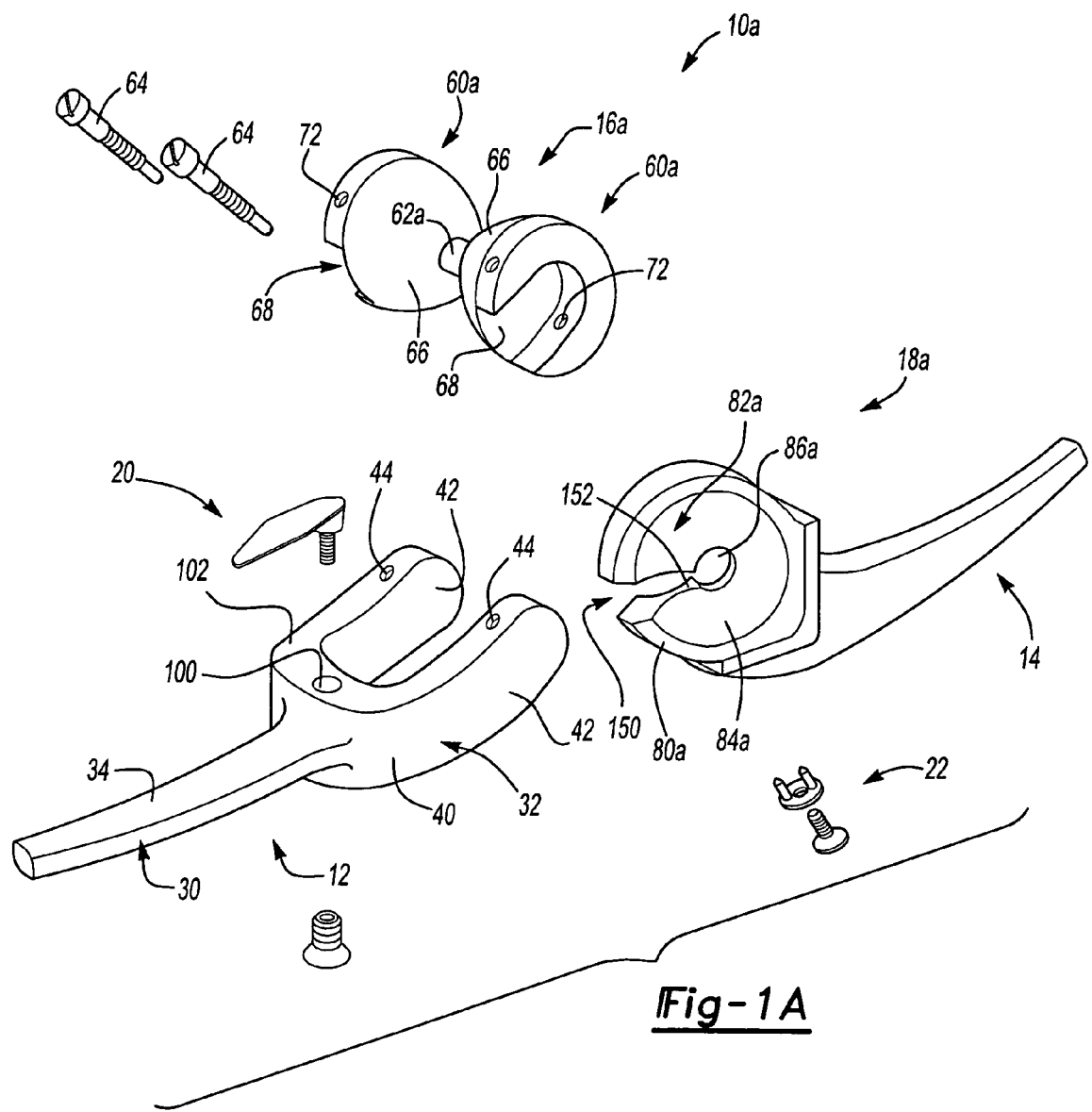
FIG. 1A is an exploded perspective view of a linked prosthetic joint kit similar to that of FIG. 1 but constructed in accordance with a first alternate embodiment of the first aspect of the present teachings.

In FIG. 1A, a linked prosthetic joint device constructed in accordance with the teachings of an alternate embodiment of the first aspect of the present teachings is generally indicated by reference numeral 10a. Linked prosthetic joint 10a is shown to include first stem structure 12, second stem structure 14, first bearing component 16a, second bearing component 18a, modular flange 20 and tissue fastener 22.

First bearing component 16a is similar to first bearing component 16 in all respects except that it is unitarily formed. Accordingly, pin portion 62a is not removable form condyle portions 60a. Second bearing component 18a is similar to second bearing component 18 in all respects except that an insertion aperture 150 extends form through hole 86a outwardly through bearing member 82a and cage portion 80a. Accordingly, insertion aperture 150 renders the area of second bearing surface 84a somewhat smaller than second bearing surface 84. Second bearing surface 84a is otherwise identical to second bearing surface 84.

To use linked prosthetic joint device 10a, first and second stem structures 12 and 14 are initially inserted to the humerus and ulna and first bearing component 16a is fastened to the first stem structure 12 using techniques similar to that discussed above for prosthetic joint device 10. First bearing component 16a is then positioned adjacent second bearing component 18a such that pin portion 62a is in insertion aperture 150. Pin portion 62a is then forced toward through hole 86a. The distal end 152 of insertion aperture 150 is smaller than pin portion 62a to permit bearing member 82a to engage pin portion 62a in a snap fit manner, so as to inhibit the unintentional withdrawal of pin portion 62a from through hole 86a. As discussed above, through hole 86a is preferably larger in diameter than pin portion 62a. At this point, first and second bearing components 16a and 18a hingedly couple first and second stem structures 12 and 14 together in a linked manner.

Figure 4:
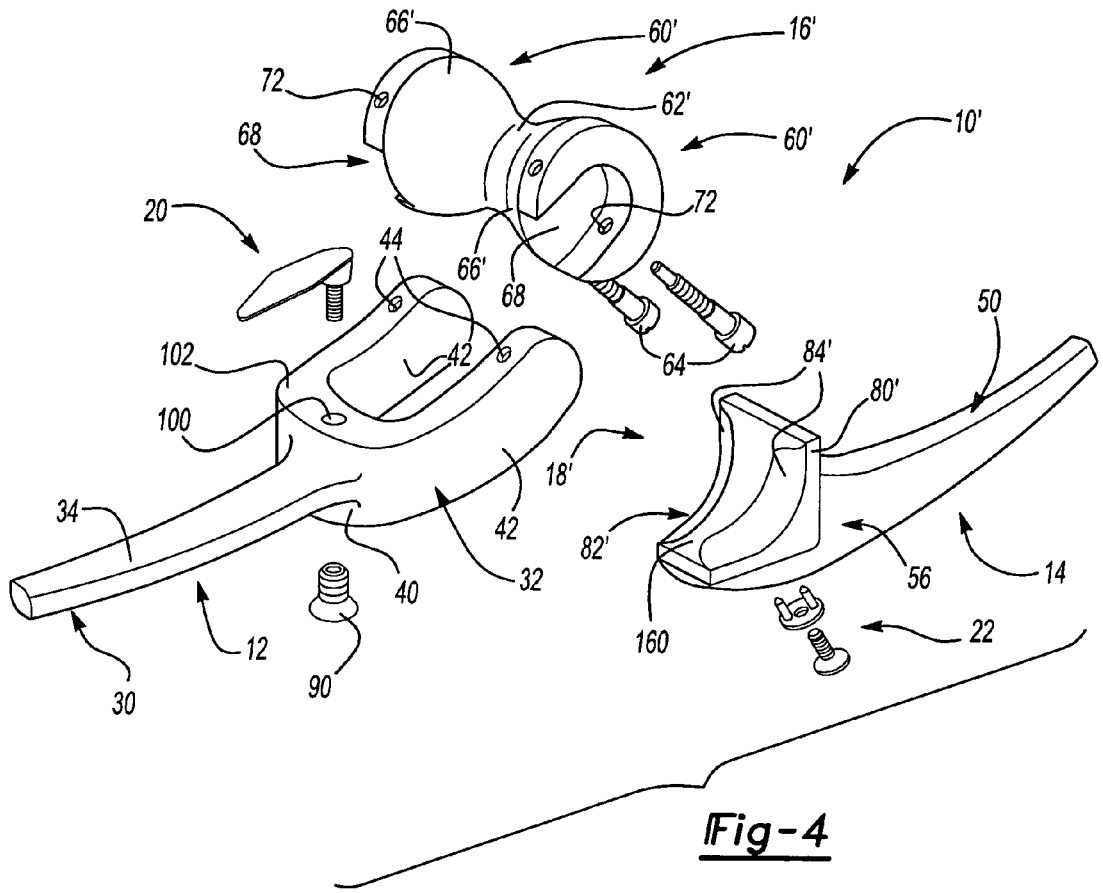
FIG. 4 is an exploded perspective view of an unlinked prosthetic joint kit constructed in accordance with the teachings of a first aspect of the present teachings.
Figure 5:
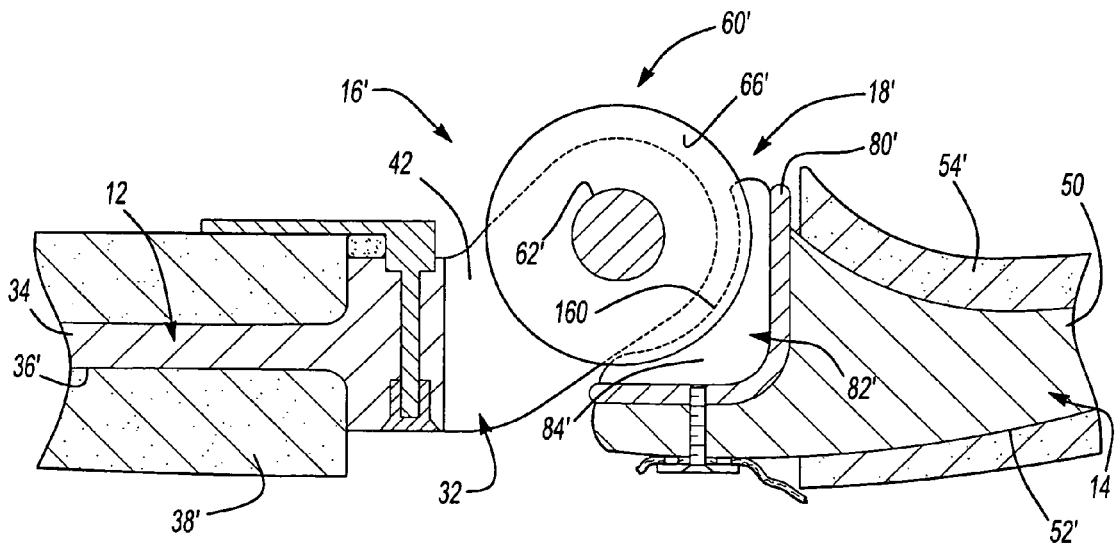
FIG. 5 is a longitudinal cross-sectional view of the unlinked prosthetic joint kit of FIG. 4 implanted in the arm of a person.

In FIGS. 4 and 5, an unconstrained or unlinked prosthetic joint device constructed according to a first aspect of the present teachings is generally indicated by reference number 10'. Unlinked prosthetic joint 10' is shown to include a first stem structure 12, a second stem structure 14, a first bearing component 16', a second bearing component 18', a modular flange 20 and a tissue fastener 22. Unlinked prosthetic joint 10' is shown to be operatively associated with a humerus 38' and an ulna 54' (FIG. 5), but those skilled in the art will understand that the teachings of the present teachings have application to prosthetic joints for other applications and as such, the scope of the present teachings will not be limited to elbow joints.

First bearing component 16' is similar to first bearing component 16 in that it includes a pair of condyle portions 60' and a pin portion 62'. However, first bearing component 16' is preferably unitarily formed with pin portion 62' extending between the spherically-shaped bearing portions 66' and fixedly coupling the spherically-shaped bearing portions 66' thereto. Like first bearing component 16, each of the condyle portions 60' of first bearing component 16' includes a slotted aperture 68 and a fastener aperture 72. Spherically shaped bearing portions 66' collectively form a first bearing surface. Like first bearing component 16, first bearing component 16' may be made from any appropriate bearing material, such as cobalt chromium alloy.

Second bearing component 18' is similar to second bearing component 18 in that it includes a cage portion 80' which is fixedly coupled to the proximal portion 56 of second stem structure 14 and a bearing member 82' which is fixedly coupled to the cage portion 80'. For purposes of clarity, bearing member 82' has not been shown in cross section in FIG. 5. Bearing member 82' includes spherical bearing surfaces 84' which are adapted to engage the spherically-shaped bearing portions 66' of the condyle portions 60'. The pair of bearing surfaces 84' collectively form a second bearing surface that mates with the first bearing surface. Bearing member 82' also includes a raised portion 160 which is adjacent the spherical bearing surfaces 84' and configured to clear pin portion 62', preferably without transmitting load therebetween (i.e., pin portion 62' preferably does not contact the surfaces of raised portion 160). In the particular embodiment illustrated, bearing member 82' is fabricated from polyethylene which has been molded to cage portion 80. Alternatively, bearing member 82' may be fabricated from any other appropriate material such as a cobalt chromium alloy, ceramics, or stainless steel.

To use unlinked prosthetic joint 10', first stem structure 12 is implanted in humerus 38' such that proximal portion 34 is located in the medullary canal 36' as shown in FIG. 5. Second stem structure 14 is similarly implanted in ulna 54' such that distal portion 50 is located in the medullary canal 52'. First bearing component 16' is next positioned adjacent the distal portion 32 of first stem structure 12 and furcations 42 are engaged to slotted apertures 68. Fasteners 64 are inserted through their respective mounting apertures 72 and threadably engaged to their threaded fastener aperture 44. When fully seated, each of the fasteners 64, extends through its respective furcation 42 to prevent its associated condyle portion 60' from rotating relative to thereto. The proximal end of the ulna 54' is positioned adjacent the distal end of the humerus 38' such that the pin portion 62' is proximate the raised portion 160 and the spherically-shaped bearing portions 66' of the condyle portions 60' engage the spherical bearing surface 84'. At this point, first and second bearing components 16' and 18' are coupled together in an unconstrained or unlinked manner (i.e., held in position by the soft tissues of the elbow). Construction of unlinked prosthetic joint 10' in this manner provides many of the same advantages as mentioned above for linked prosthetic joint 10, such as the ability of first and second bearing surfaces 16' and 18' to spread out the load that is transmitted through unlinked prosthetic joint 10' over a relatively large area, rather than concentrate the load at a single point or over a line of contact to thereby improve the durability of unlinked prosthetic joint 10'.

As a surgeon may not always know prior to beginning an operation whether a patient would be better served by a linked or an unlinked joint prosthesis and as it is also occasionally necessary to convert an unlinked joint prosthesis to a constrained joint prosthesis, or vice versa, after implementation and use for a period of time, it is highly desirable that the joint prosthesis be modular so as to provide the surgeon with a high degree of flexibility which may be achieved in a relatively simple and cost-effective manner.

Figure 6:
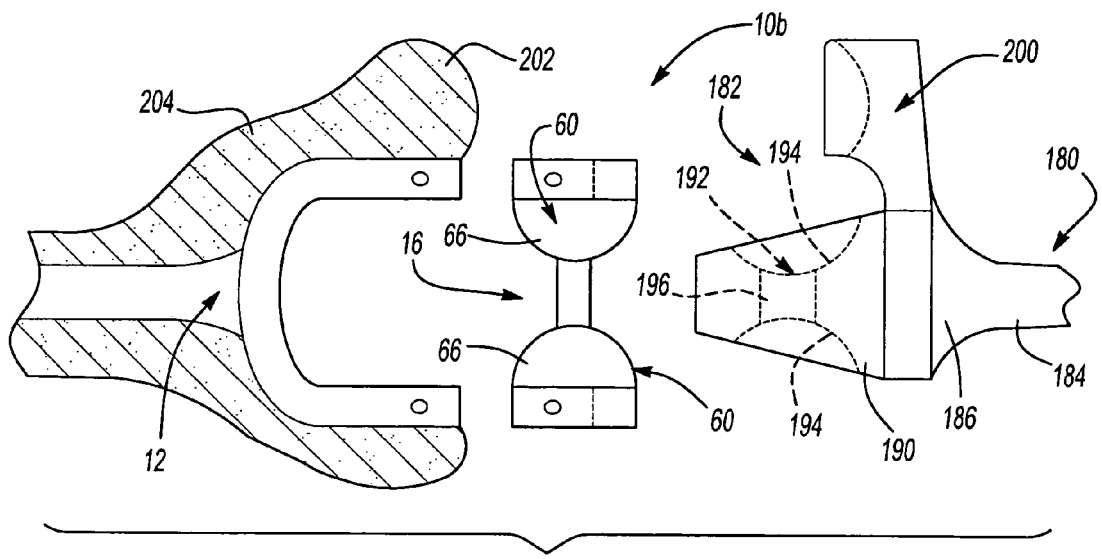
FIG. 6 is an exploded plan view of a linked prosthetic joint kit constructed in accordance with a second alternate embodiment of the first aspect of the present teachings.
Figure 7:
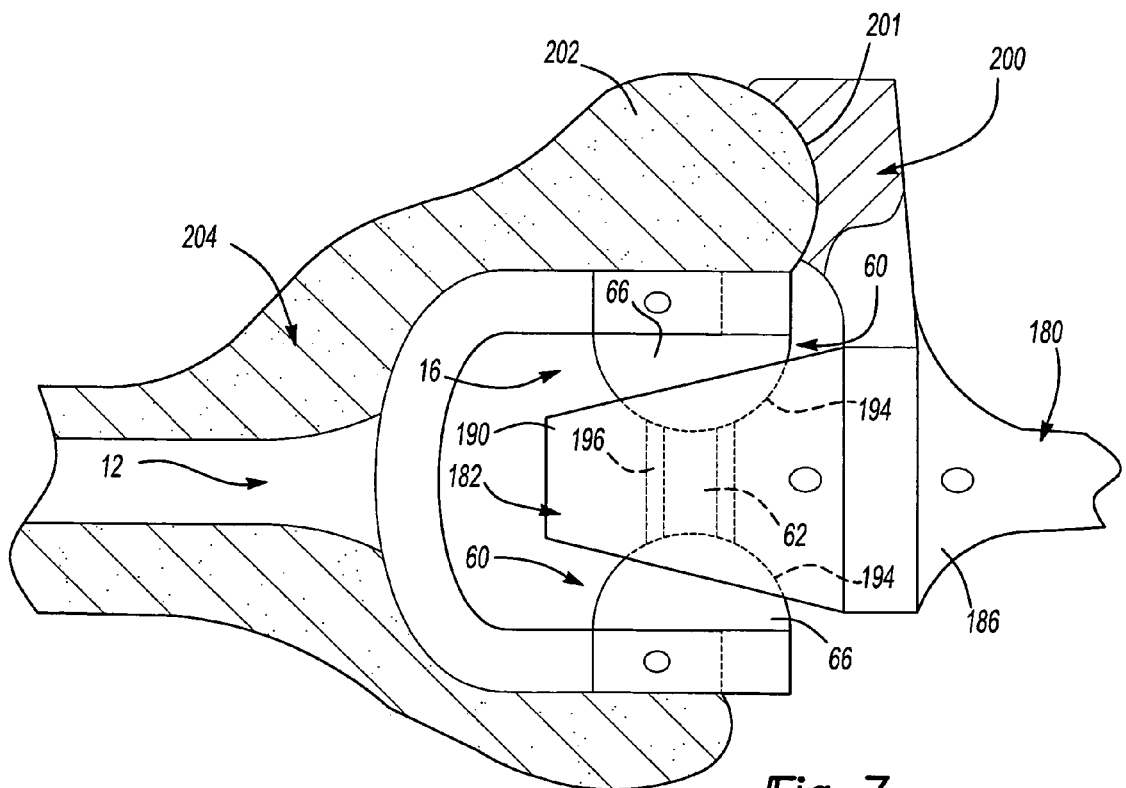
FIG. 7 is an enlarged portion of the linked prosthetic joint kit of FIG. 6.

In FIGS. 6 and 7, a linked prosthetic joint constructed in accordance with a second aspect of the present teachings is generally indicated by reference numeral 10b. Linked prosthetic joint 10b is shown to include first stem structure 12, a third stem structure 180, first bearing component 16, a third bearing component 182. Third stem structure 180 is similar to second stem structure 14 in that it includes a distal portion 184 which is adapted to fit within the medullary canal of an ulna. The proximal portion 186 of third stem structure 180 is coupled to third bearing component 182.

Third bearing component 182 is similar to second bearing component 18 in that it includes a cage portion 190 and a bearing member 192. Cage portion 190 is fixedly coupled to the proximal portion 186 of third stem structure 180. Bearing member 192 is fixedly coupled to cage portion 190. Bearing member 192 includes a pair of spherical bearing surfaces 194 which are configured to engage the spherically-shaped bearing portions 66 of the condyle portions 60 and a through hole 196 which is configured to receive pin portion 62, preferably without transmitting load therebetween (i.e., pin portion 62 preferably does not contact the surfaces of through hole 196). Bearing member 182 also includes a lateral buttress 200. Lateral buttress 200 includes a supplementary bearing surface 201 which is configured for receiving a capitellum 202 of the humerus 204. In the particular embodiment illustrated, third bearing component 182 is fixedly coupled to third stem structure 180 and as such, the combination of the second stem structure 14 and second bearing component 18 is interchangeable with the combination of the third stem structure 180 and the third bearing component 182. However, those skilled in the art will understand that second and third bearing components 18 and 182 may also be releasably coupled to a stem structure, thereby eliminating the need for a third stem structure 180 which would otherwise be identical to second stem structure 14. Those skilled in the art will also understand that the lateral butress may alternatively be coupled directly to the third stem structure 180, being either releasably attached thereto or integrally formed therewith.

Figure 8:
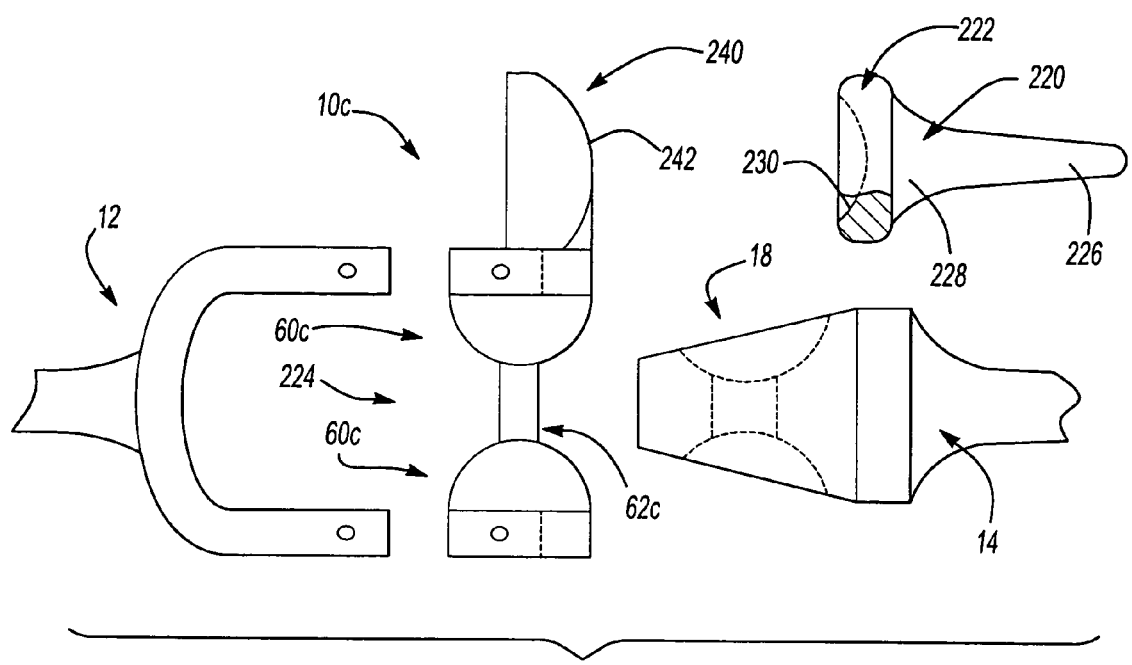
FIG. 8 is an exploded plan view of a linked prosthetic joint kit constructed in accordance with a third alternate embodiment of the first aspect of the present teachings.

In FIG. 8, another linked prosthetic joint constructed in accordance with the teachings of a second aspect of the present teachings is generally indicated by reference numeral 10c. Linked prosthetic joint 10c is shown to include first stem structure 12, second stem structure 14, a fourth stem structure 220, second bearing component 18, a fourth bearing component 222 and a fifth bearing component 224. Fourth stem structure 220 includes a distal end 226 which is adapted to fit within the medullary canal of a radius and a proximal end 228 which is fixedly coupled to fourth bearing component 222. Fourth bearing component 222 includes a fourth bearing surface 230.

Fifth bearing component 224 is similar to first bearing component 16 in that it includes, for example, a pair of condyle portions 60 and a pin portion 62 which permits first and fifth bearing components 16 and 224 to be interchangeable. However, fifth bearing component 224 also includes a lateral extension 240 which is adapted to replace at least a portion of the capitellum of the humerus. Lateral extension 240 defines a fifth bearing surface 242 which is configured to mate with fourth bearing surface 230. Preferably, at least a portion of each of the fourth and fifth bearing surfaces 230 and 242 is spherically shaped to permit loads transmitted therebetween to be spread out over a relatively large area, rather than be concentrated at a single point or along a line of contact.

Figure 9:
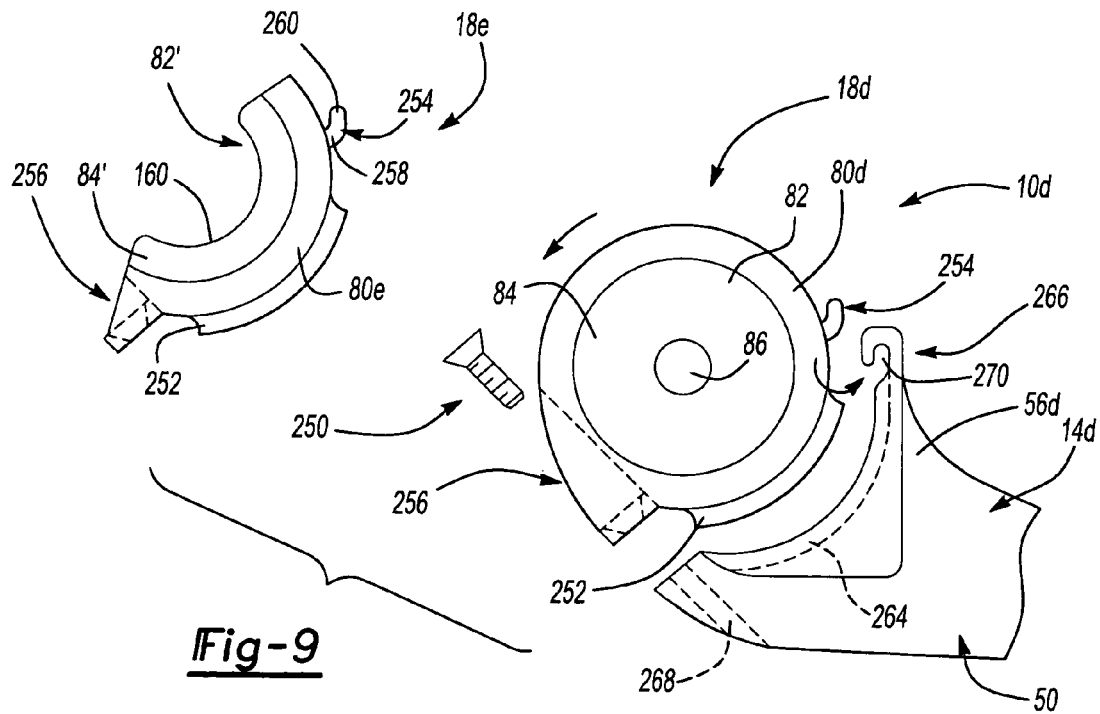
FIG. 9 is a exploded side elevation view of a portion of a joint kit constructed in accordance with the teachings of a second aspect of the present teachings.

In FIG. 9, a portion of a modular prosthetic joint kit constructed in accordance with the teachings of a second aspect of the present teachings is generally indicated by reference numeral 10d. Modular prosthetic joint kit 10d is shown to include second stem structure 14d, second bearing component 18d, second bearing component 18e and a fastener 250.

Second bearing components 18d and 18e are similar to second bearing components 18 and 18', respectively, but are shown to be separable from second stem structure 14d. Second bearing components 18d and 18e also include a keel member 252, a clip member 254 and a fastener aperture 256 which are formed in cage portions 80d and 80e, respectively. Keel member 252 extends circumferentially around at least a portion of the perimeter of each of the cage portions 80d and 80e between clip member 254 and fastener aperture 256. Clip member 254 includes a first portion 258 which extends generally perpendicularly outward from its associated cage portion and a second portion 260 which is coupled to the distal end of first portion 258. Second portion 260 extends generally outwardly and away from first portion 258. Fastener aperture 256 is located across from clip member 254 and is sized to receive fastener 250.

Second stem structure 14d is similar to second stem structure 14 in that it includes a distal end 50 which is adapted to fit within the medullary canal of an ulna. Second stem structure 14d also includes a proximal portion 56d having a keel slot 264, a hook structure 266 and an internally threaded fastener aperture 268. Keel slot 264 is a slot that is sized to receive keel member 252 in a slip fit manner. Keel slot 264 and keel member 252 cooperate to resist relative mediallateral motion of cage portion (e.g. 80d) relative to second stem structure 14d. Hook member 266 is generally U-shaped and defines a clip aperture 270 which is sized to receive clip member 254.

To use modular prosthetic joint kit 10d, the distal end 50 of second stem structure 14d is inserted in the medullary canal of the ulna. The modularity of the prosthetic joint kit 10d permits the surgeon to assess the patient's elbow to determine if the patient would be better served by a linked or an unlinked joint prosthesis. Once a decision has been made as to which type of joint prosthesis would better serve the patient, the surgeon selects an appropriate one of the second bearing components 18d and 18e, places its clip member 254 into the clip aperture 270, pivots the cage portion (i.e. 80d) toward the proximal end 56d of the second stem structure 14d to engage the keel member 252 into the keel slot 264, inserts the fastener 250 through the fastener aperture 256 and threadably engages the fastener 250 to the internally threaded fastener aperture 268 to fixedly but releasably couple the second stem structure 14d with the selected one of the second bearing components 18d and 18e.

Figure 10:
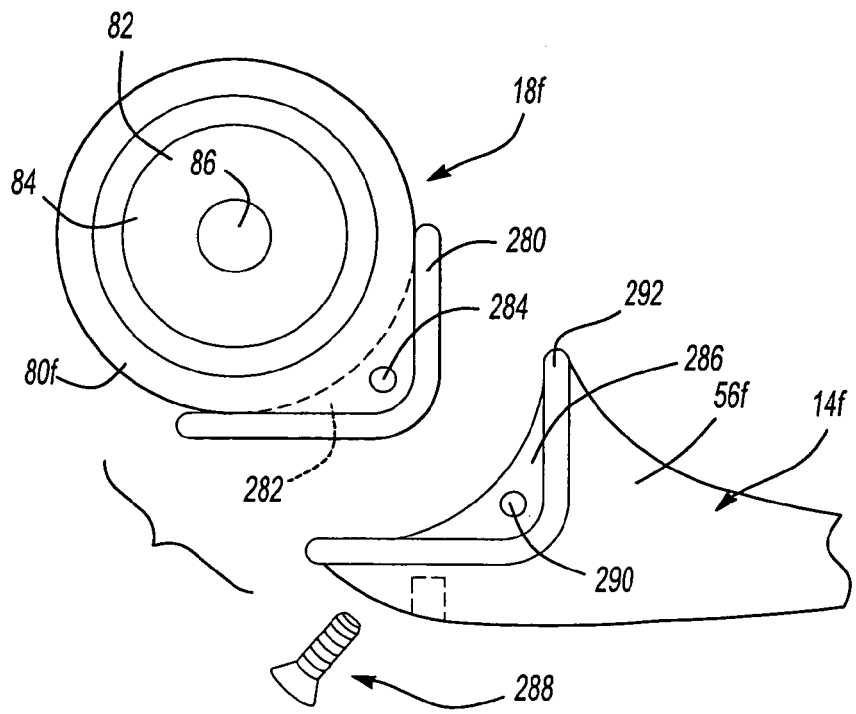
FIG. 10 is an exploded side elevation view of a portion of a joint kit constructed in accordance with a first alternate embodiment of the second aspect of the present teachings.

Those skilled in the art will understand that second bearing components 18d and 18e may be coupled to second stem structure 14d in various other manners as illustrated in FIGS. 10 through 15. In FIG. 10, second bearing component 18f is shown to include a generally L-shaped tray portion 280 which is fixedly coupled to cage portion 80f. Tray portion 280 includes a keel slot 282 and a fastener aperture 284. Keel slot 282 is operable for receiving a keel member 286 formed into the proximal end 56f of second stem structure 14f. Fastener aperture 284 is operable for receiving a fastener 288 which may be threadably engaged to an internally-threaded fastener aperture 290 in the proximal end 56f of second stem structure 14f to thereby permit second bearing component 18f and second stem structure 14f to be fixedly but releasably coupled.

When coupled together, keel slot 282 and keel member 286 cooperate to resist relative medial-lateral motion of cage portion 80f relative to second stem structure 14f. Additionally, tray portion 280 cooperates with an L-shaped flange 292 to which it abuts to further resist relative rotation between second stem structure 14f and cage portion 80f.

Figure 11:
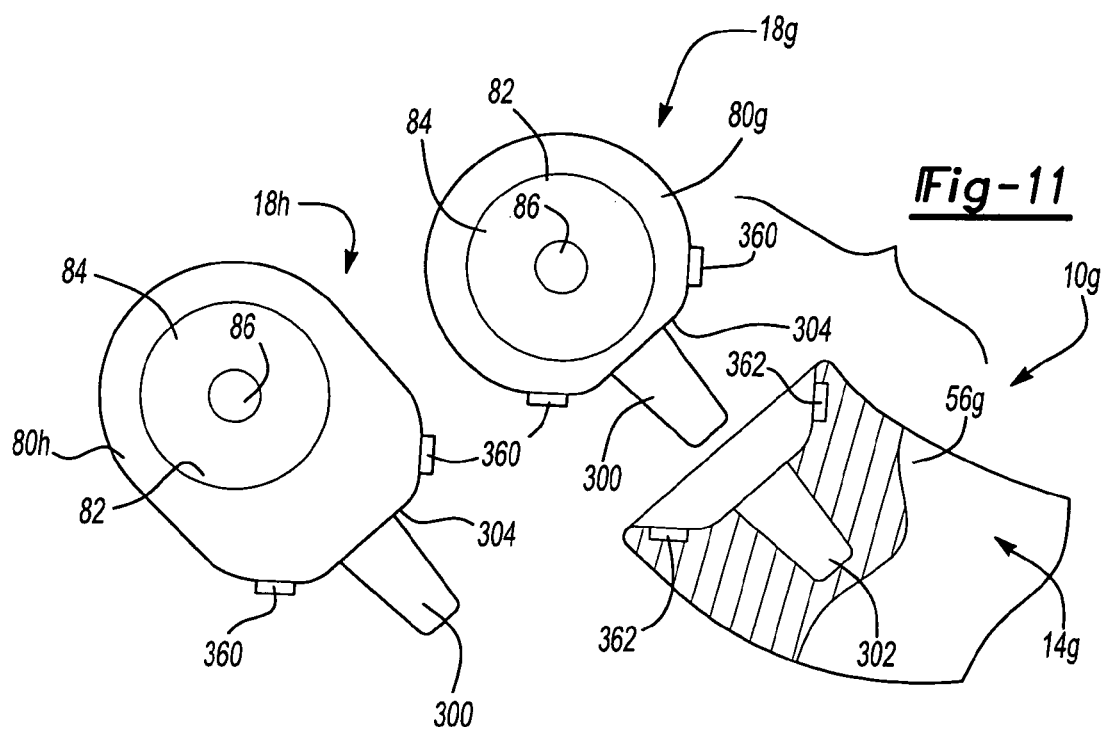
FIG. 11 is an exploded side elevation view of a portion of a joint kit constructed in accordance with a third alternate embodiment of the second aspect of the present teachings.
Figure 12:
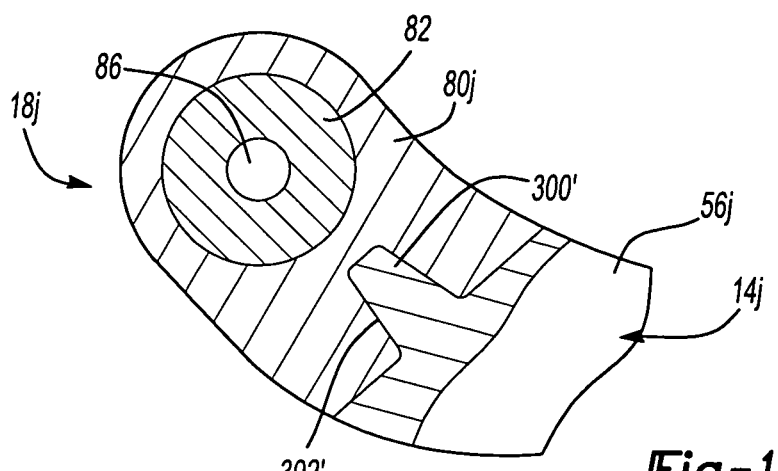
FIG. 12 is a longitudinal cross-sectional view of a portion of a joint kit constructed in accordance with a fourth alternate embodiment of the second aspect of the present teachings.

In FIG. 11, second bearing components 18g and 18h are shown to include a stem member 300 which extends from their respective cage portions 80g and 80h. Stem member 300 is engageable with a stem aperture 302 formed into the proximal end 56g of second stem structure 14g. As shown in FIG. 12, stem member 300' may alternatively be incorporated into the proximal end 56j of second stem structure 14j and stem aperture 302' may be formed into cage portion 80j of second bearing component 18j.

To provide the surgeon with additional flexibility, second bearing component 18h is shown in FIG. 11 to be slightly longer than second bearing component 18g (i.e. the distances from the centerline of bearing member 82 to the confronting surface 304 of their respective cage portions 80g and 80h is shorter for second bearing component 18g). This variation between second bearing components 18g and 18h permits the surgeon to adjust the length of prosthesis 10g to take into account the physical characteristics of the patient's arm.

Figure 13:
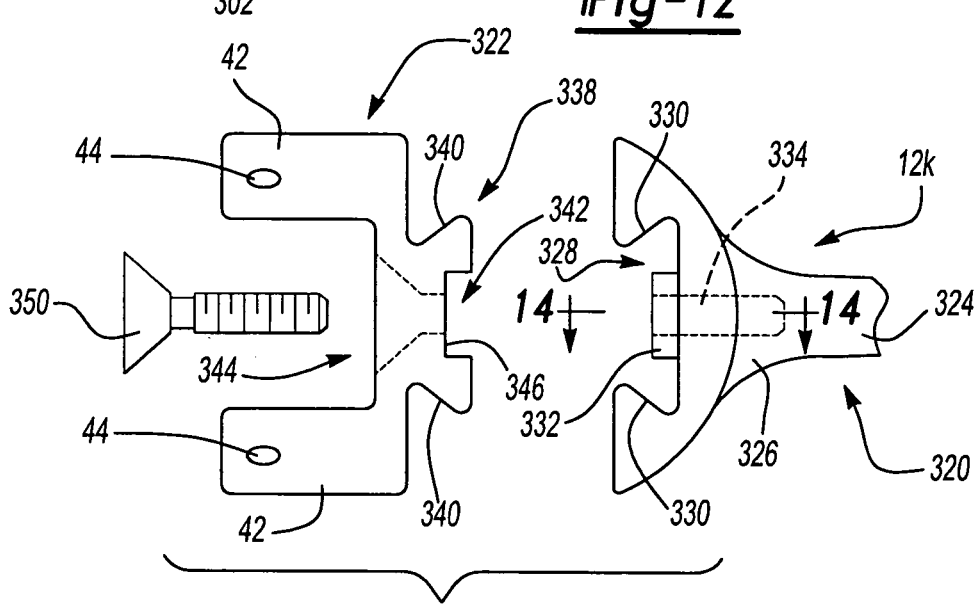
FIG. 13 is an exploded side elevation view of a portion of a joint kit constructed in accordance with a fifth alternate embodiment of the second aspect of the present teachings.
Figure 14:
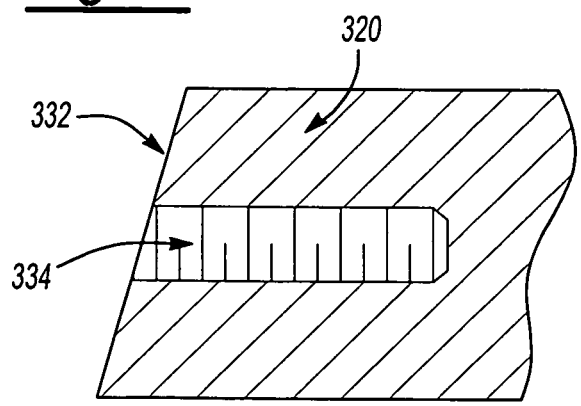
FIG. 14 is a cross-sectional view taken along the line 14-14 of FIG. 13.

Modularity may also be incorporated into first stem structure 12k as shown in FIGS. 13 and 14. First stem structure 12k is shown to include a stem member 320 and a yoke member 322. The proximal end 324 of stem member 320 is adapted to fit within the medullary canal of a humerus and the distal end 326 of stem member 320 terminates at a dovetail aperture 328 having a pair of inwardly tapering walls 330 and a tapered retaining wedge 332. An internally threaded fastener aperture 334 extends through retaining wedge 332. Yoke member 322 is shown to be similar to the distal end 32 of first stem structure 12 as it includes furcations 42 and threaded fastener apertures 44. Yoke member 322 also includes a dovetail member 338 having a pair of outwardly tapering surfaces 340, a wedge slot 342 and a through hole 344. Dovetail member 338 is configured to mate with dovetail aperture 328 such that engagement of retaining wedge 332 to the upper surface 346 of wedge slot 342 forces tapered surfaces 340 against a respective one of the inwardly tapering walls 330. A fastener 350 is inserted through hole 344 and threadably engaged to internally threaded fastener aperture 334 to fixedly but releasably couple yoke member 322 and stem member 320 together.

Referring back to FIG. 11, second bearing components 18g and 18h are also shown to include a pair of tang members 360. Each of the tang members 360 extends outwardly from its respective cage portion (i.e., 80g) and in the particular embodiment illustrated, is generally rectangularly shaped. Each of the tang members 360 is sized to engage a tang recess 362 in the proximal end 56g of the second stem structure 14g. Engagement of the tang members 360 into their respective tang recess 362 inhibits relative rotation between the second stem structure 14g and the second bearing components 18g and 18h.

Figure 15:
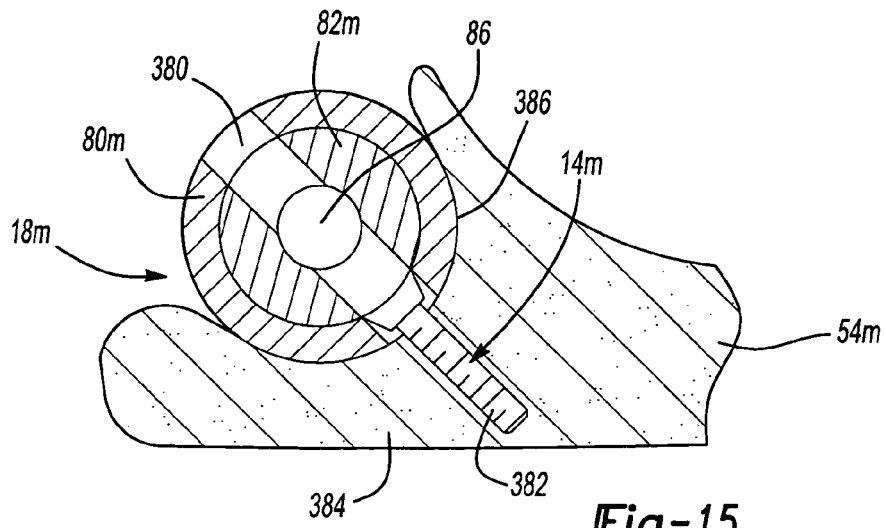
FIG. 15 is a cross-sectional view of a portion of a joint kit constructed in accordance with a sixth alternate embodiment of the second aspect of the present teachings.

In FIG. 15, second bearing component 18m is shown to have a fastener aperture 380 which is formed through a bearing member 82m and cage portion 80m. Second stem structure 14m, which is a threaded fastener 382 in this embodiment, is disposed through the fastener aperture 380 in second bearing component 18m and threadably engaged to the cancellous bone 384 of the ulna 54m. Construction in this manner is advantageous in that it permits the extent of the trauma experienced by the patient to be minimized. To further this goal, the distal end 386 of cage portion 80m is shown to be generally cylindrically shaped so as to minimize the amount of bone that must be removed to prepare the ulna 54m for the second bearing component 18m.

Figure 16:
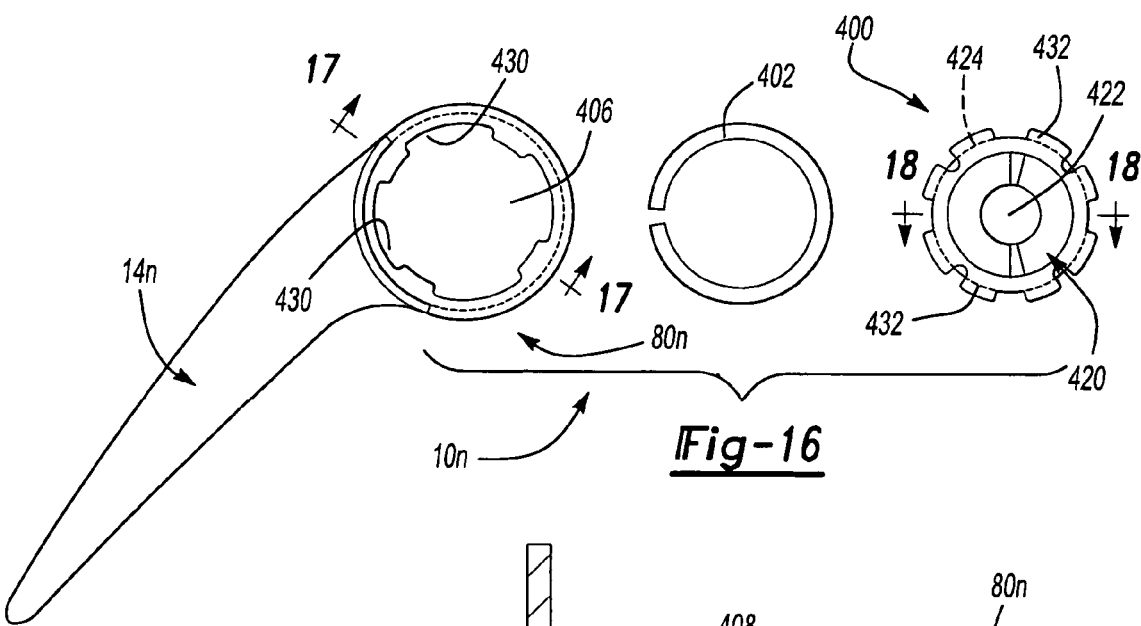
FIG. 16 is an exploded side elevation view of a portion of linked prosthetic joint kit constructed in accordance with the teachings of various embodiments of a third aspect of the present teachings.
Figure 17:
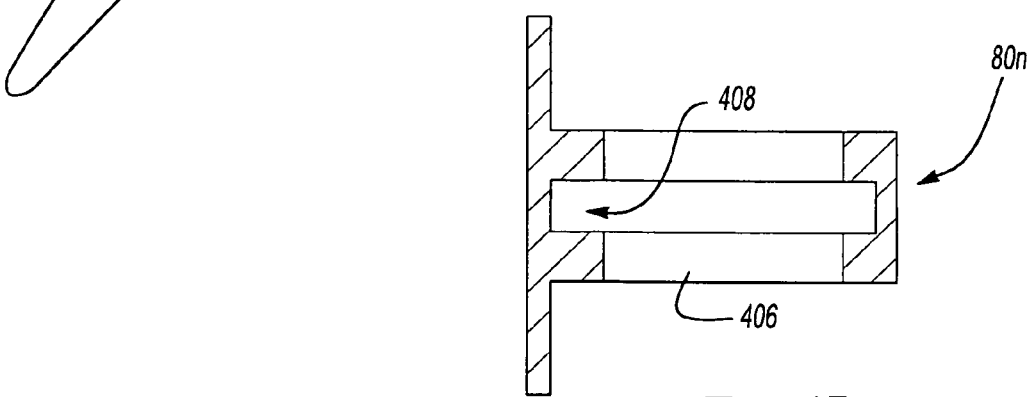
FIG. 17 is a cross-sectional view taken along the line 17-17 of FIG. 16.
Figure 18:
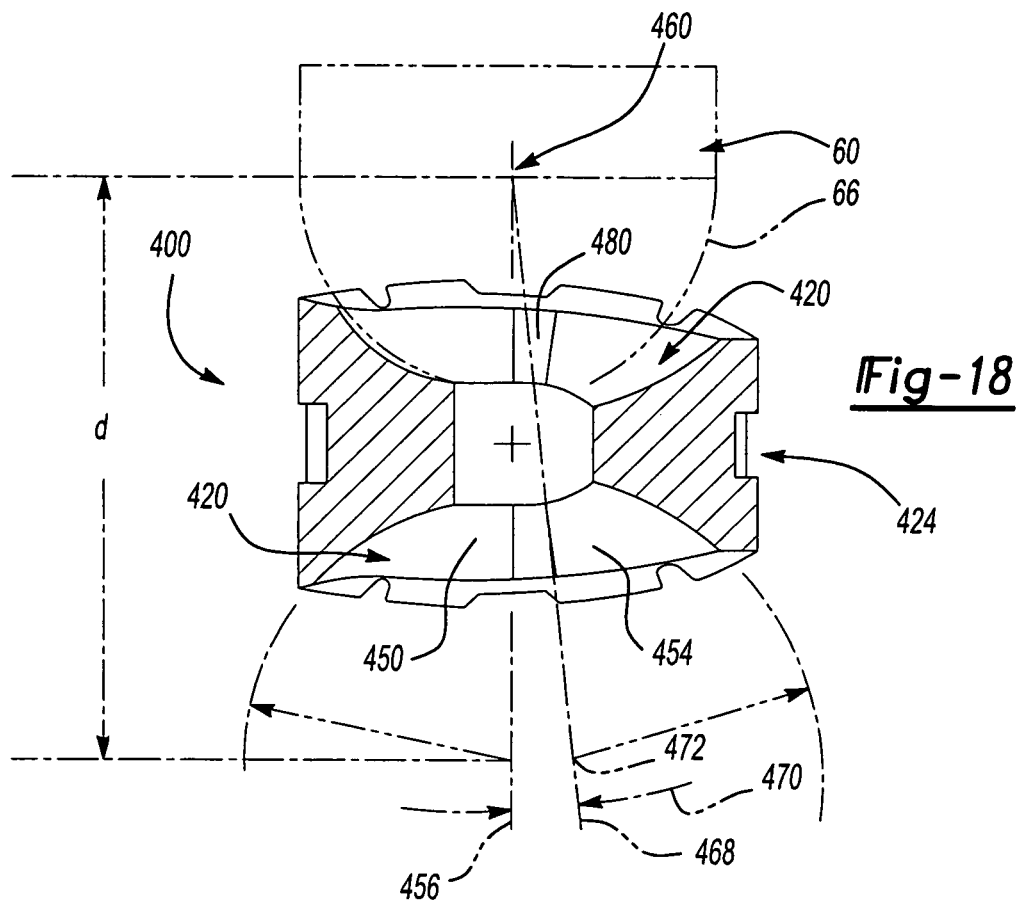
FIG. 18 is a cross-sectional view taken along the line 18-18 of FIG. 16.

In FIGS. 16 through 18, a portion of a modular prosthetic joint kit constructed in accordance with the teachings of a third aspect of the present teachings is generally indicated by reference numeral 10n. Modular prosthetic joint kit 10n is shown to include a bearing insert 400, a retaining ring 402 and a second stem structure 14n having an integrally attached cage portion 80n. Cage portion 80n is shown to include a bearing aperture 406 for receiving bearing insert 400. In the particular embodiment illustrated, cage portion 80n also includes a circumferentially extending first ring groove 408 formed along the perimeter of bearing aperture 406 and operable for receiving a first portion of retaining ring 402.

Bearing insert 400 is generally cylindrically shaped, having a pair of spherical depressions 420 which collectively form a bearing surface that is configured to mate with the spherically-shaped bearing portions 66 of the first bearing component 16. Bearing insert 400 also includes a through hole 422 which is adapted to receive pin portion 62, preferably without transmitting load therebetween. A circumferentially extending second ring groove 424 is formed in the outer perimeter of bearing insert 400, the second ring groove 424 being operable for receiving a second portion of retaining ring 402. Construction in this manner is advantageous in that the surgeon may select a bearing insert 400 from a plurality of bearing inserts 400 to adapt prosthetic joint 10n to the patient.

In the particular embodiment illustrated, bearing aperture 406 is shown to include a plurality of radially outwardly extending tab apertures 430 and bearing insert 400 is shown to include a plurality of radially outwardly extending tabs 432. If desired, a first one of the tab apertures 430 and a first one of the tabs 432 may be sized differently than the remaining tab apertures 430 and tabs 432, respectively, to key the bearing insert 400 to a specific orientation relative to second stem structure 14n.

With specific reference to FIG. 18, each of the pair of spherical depressions 420 includes a first spherical portion 450 and a second spherical portion 454. Each of the first spherical portions 450 are formed into bearing insert 400 along an axis 456 that is coincident with the longitudinal centerline of the bearing insert 400. Each of the first spherical portions 450 are formed by a spherical radius approximately equal in magnitude to the spherical radius which defines the spherically-shaped bearing portion 66 of each of the condyle portions 60 of first bearing component 16. The distance between the spherical radii along axis 456 is equal to a predetermined distance, d.

The centerpoint 456 of the spherical radius that defines one of the first spherical portions 450 is employed to generate the second spherical portion 454 on the opposite face of the bearing surface. A second centerline 468 is constructed from centerpoint 460 toward the opposite face at a predetermined constraint angle 470, such as 3.5 degrees. The spherical radius that defines the second spherical portion 454 on the opposite face is generated from a second centerpoint 472 which is positioned along the second centerline 468 at a distance d from centerpoint 460. Construction of bearing insert 400 in this manner permits first bearing component 16 to rotate about centerline 456, as well as to pivot relative to bearing insert 400 about the spherically-shaped bearing portion 66 of each of the condyle portions 60.

A transition zone 480 is formed between each of the first and second spherical portions 450 and 454 wherein a radius is formed at the intersection of the radii which define the first and second spherical portions 450 and 454 to "soften" the transition between the first and second spherical portions 450 and 454 to render the movement of the condyle portions 60 over the first and second spherical portions 450 and 454 more comfortable to the patient.

Those skilled in the art will understand that the degree of the constraint may be defined by the constraint angle. Accordingly, modular prosthetic joint kit 10n preferably includes a plurality of bearing inserts 400, each having a bearing surface with a second spherical portion 454 that is defined by a different constraint angle. Those skilled in the art will also understand that the degree of the constraint may be additionally or alternatively defined by a constraint characteristic, which is illustrated in FIGS. 19A through 19D.

Figure 19A:
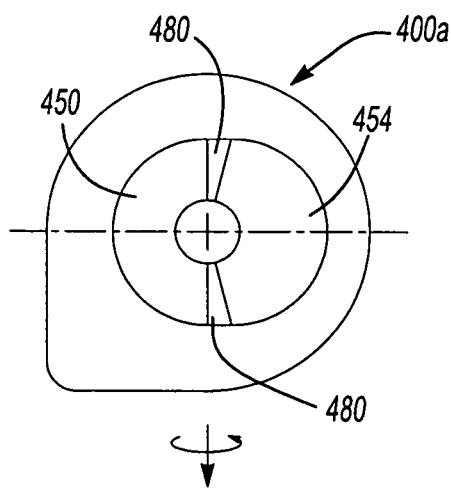
FIG. 19A through 19D are side elevation views of bearing inserts constructed with varying degrees of varus/valgus constraint.
Figure 19B:
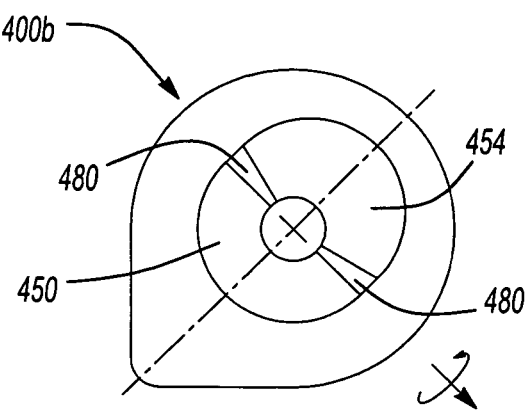
Figure 19C:
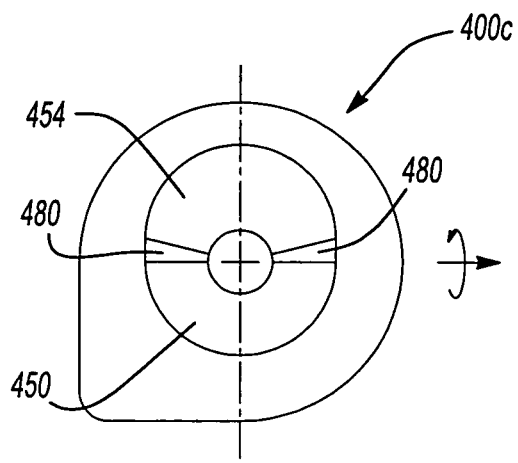
Figure 19D:
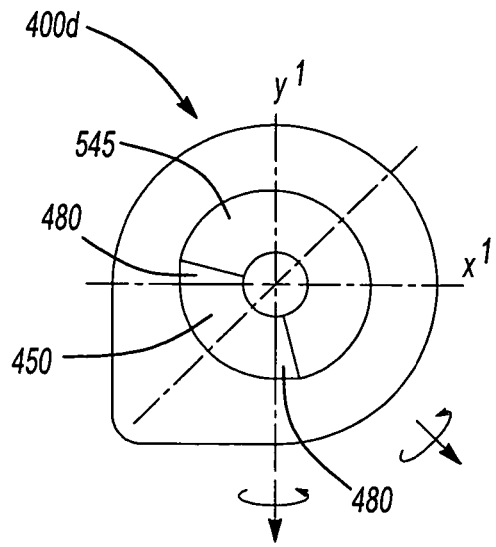

In FIG. 19A, bearing insert 400a has a first predetermined constraint characteristic orientation wherein the centerlines which define the radii which define first and second spherical portions 450 and 454 are contained in a plane which is generally perpendicular to the longitudinal axis of the ulna. Construction of bearing insert 400a in this manner provides a varying degree of axial constraint. In FIG. 19B, bearing insert 400b has a second predetermined constraint characteristic wherein the centerlines which define the radii which define first and second spherical portions 450 and 454 are contained in a plane which is at approximately 45° to the longitudinal axis of the ulna. Construction of bearing insert 400b in this manner provides a varying degree of a combination of axial and varus/valgus constraint. In FIG. 19C, bearing insert 400c has a third predetermined constraint characteristic wherein the centerlines which define the radii which define first and second spherical portions 450 and 454 are contained in a plane which is generally parallel the longitudinal axis of the ulna. Construction of bearing insert 400c in this manner provides a varying degree of varus/valgus constraint. In FIG. 19D, bearing insert 400d is constructed in a manner that is generally similar to that of bearing inserts 400a, 400b and 400c except that the constraint angle employed to construct bearing insert 400d is rotated form point x1 to y1 as indicated in FIG. 19d. As a result, there is no single line of orientation in which the constraint is limited. Construction of bearing insert 400d in this manner provides a varying degree of constraint in both an axial direction and a varus/valgus direction.

In FIGS. 20A through 22, a portion of a modular prosthetic joint kit constructed in accordance with the teachings of an alternate embodiment of the third aspect of the present teachings is generally indicated by reference numeral 10p. Modular prosthetic joint kit 10p is similar to modular prosthetic joint kit 10n in that it includes a bearing insert 400p and a second stem structure 14p having a integrally attached cage portion 80p.

Cage portion 80p is shown to include a bearing aperture 406p for receiving bearing insert 400p. In the particular embodiment illustrated, cage portion 80p includes a plurality of tab apertures 430p, a plurality of tab slots 500 and a hook structure 502. Each of the tab apertures 430p extends axially through cage portion 80p and circumferentially around a portion of bearing aperture 406p. Each of the tab slots 500 intersects one of the tab apertures 430p and extends circumferentially around a portion of bearing aperture 406p away from its associated tab aperture 430p. Hook structure 502 is adjacent one of the tab apertures 430p and extends radially inwardly and circumferentially around a portion of bearing aperture 406p. A clip slot 510 is formed circumferentially through hook structure 502.

Bearing insert 400p is generally similar to bearing insert 400 except for the configuration of the plurality of tabs 432p and the incorporation of a clip structure 520 into a bearing body 522. Each of the plurality of tabs 432p is relatively thin and do not extend axially across bearing insert 400p. This permits the tabs 432p of bearing insert 400p to be aligned to a tab aperture 430p and bearing insert 400p to be rotated so that each of the tabs 432p is disposed within one of the tab slots 500 to thereby prevent bearing insert 400p from moving in an axial direction.

Clip structure 520 is preferably a metal or plastic fabrication which is suitable for molding into bearing body 522. Clip structure 520 includes an arm structure 530 which extends from a clip body 532 and terminates at its distal end at a hook member 534. Clip structure 520 is configured and incorporated into bearing body 522 such when bearing insert 400p is rotated to engage tabs 432p into tab slots 500, arm structure 530 simultaneously engages clip slot 510 in hook structure 502. Rotation of bearing insert 400p to a predetermined rotational position relative to hook structure 502 permits hook member 534 to engage an edge 540 of hook structure 502. Arm structure 530 resiliently biases hook member 534 against edge 540, thereby inhibiting rotation of bearing insert 400p which would cause tabs 432p to disengage tab slots 500.

Figure 20A:
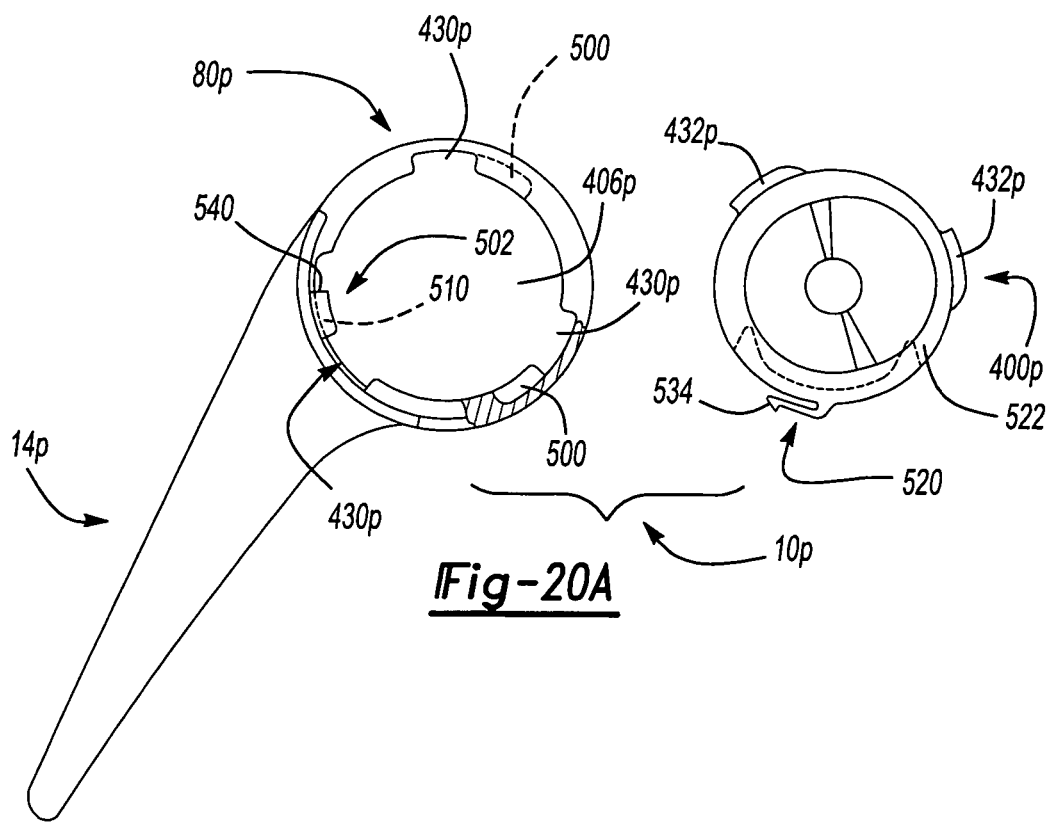
FIG. 20A is an exploded side elevation view of a portion of a linked prosthetic joint kit constructed in accordance with the teachings of a first alternate embodiment of the third aspect of the present teachings.
Figure 20B:
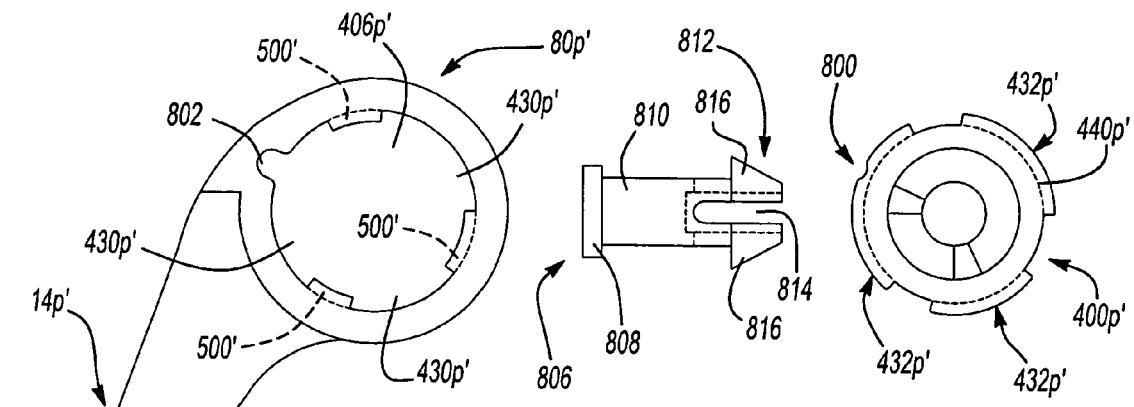
FIG. 20B is an exploded side elevation view of a portion of a linked prosthetic joint constructed in accordance with the teachings of second alternate embodiment of the third aspect of the present teachings.

In FIG. 20B, bearing insert 400p' is illustrated to be configured similarly to bearing insert 400p except that a locking aperture 800 is formed into one of the tabs 432p'. Bearing insert 400p' is inserted into bearing aperture 406p' aligned such that each of the tabs 432p' is aligned to an associated one of the tab apertures 430p'. Bearing insert 400p' is then rotated so that each of the tabs 500' is disposed within one of the tab slots 440p' and locking aperture 800 is aligned to a corresponding locking aperture 802 formed in the integrally attached cage portion 80p' of second stem structure 14p'. Engagement of tabs 500' into their respective tab slots 440p' prevents bearing insert 400p' from moving in an axial direction. Alignment of locking apertures 800 and 802 to one another permits a pin 806 to be inserted therethrough to prevent bearing insert 400p' from rotating relative to integrally attached cage portion 80p'. In the particular embodiment illustrated, pin 806 includes a head portion 808, a body portion 810 and an end portion 812. Head portion 808 has a diameter which is larger than the diameter of the hole formed by locking apertures 800 and 802. Body portion 810 is preferably smaller in diameter than the diameter of the hole formed by locking apertures 800 and 802.

A plurality of slots 814 are formed in end portion 812 which creates a plurality of fingers 816 which are flexible relative to the longitudinal axis of pin 806. Fingers 816 flex inwardly toward the longitudinal axis of pin 806 when pin 806 is inserted to locking apertures 800 and 802, eliminating the interference therebetween to permit the fingers 816 of end portion 812 to pass through integrally attached cage portion 80p' and bearing insert 400p'. Once the fingers 816 have passed through integrally attached cage portion 80p' and bearing insert 400p', they flex outwardly away from the longitudinal axis of pin 806 to inhibit the unintended withdrawal of pin 806 from locking apertures 800 and 802. Intended withdrawal of pin 806 from locking apertures 800 and 802 may be effected through the flexing of fingers 816 inwardly toward the longitudinal axis of pin 806.

Figure 20C:
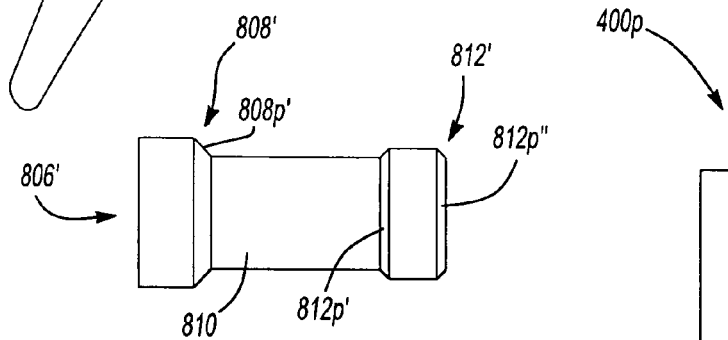
FIG. 20C is a side view of an alternately constructed pin for linking the stem structures of the second alternate embodiment of the third aspect of the present teachings.
Figure 21:
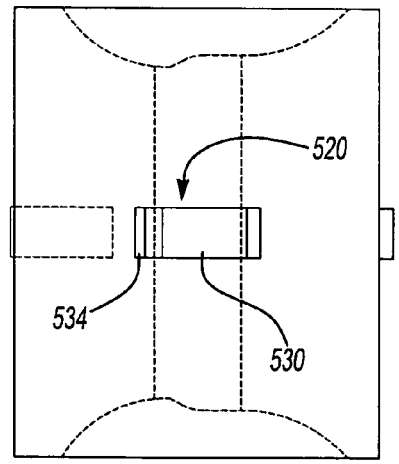
FIG. 21 is a bottom plan view of a portion of the linked prosthetic joint kit of FIG. 20A illustrating the bearing insert in greater detail.
Figure 22:
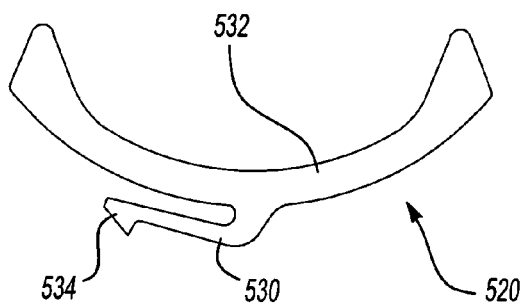
FIG. 22 is a side elevation view of a portion of the linked prosthetic joint kit of FIG. 20A illustrating the clip member in greater detail.

Those skilled in the art will understand, however, that the pin 806 for linking first and second stem structures 12 and 14p' may be constructed differently. As shown in FIG. 20C, for example, the pin 806' includes head and end portions 808' and 812' having chamfered abutting surfaces 808p' and 812p', respectively. The chamfered abutting surfaces 808p' and 812p' can abut the locking apertures 800 and 802, similar to the pin 806. As illustrated, the pin 806 in FIG. 20B includes the head portion 808 that is larger than the locking apertures 800 and 802 and the end portion 812 that can flex so that it can be smaller than the locking apertures 800 and 802 to allow passage of at least a portion of the pin 806 through the locking apertures 800, 802. One skilled in the art will understand that a locking pin can generally pass through an aperture and be held therein, through some mechanism, to allow for interconnection or locking of the various portions relative to one another. Nevertheless, the chamfered abutting surfaces 800p' and 812p' can allow for a selected engagement of a pin 806' between the locking apertures 800, 802. Additionally, the end portion 812' includes a chamfered lead portion 812p". The chamfered lead portion 812p" can assist in allowing the pin 806' to be passed through the locking apertures 800, 802. Although it will be understood that the end portion 808' can be larger than the locking apertures 800, 802 so that the pin can only pass a selected distance through the locking apertures and be held relative to the cage portion 80p' and the bearing insert 400p'. As discussed above, in relation to the locking pin 806, the leading end 812 can be allowed to pass through the locking apertures 800, 802, allowing the legs 816 to flex such that the head 812 passes through the locking apertures 800, 802, similar to the head portion 812' which is configured with the chamfered lead portion 812p" to allow for the pin 806 to pass through the locking aperture 800, 802. However, the end portion 808' is sized to not pass through the locking aperture 800, 802 so that the pin 806' can be held in a selected location. Pin 806' is installed by simply pressing it through the bearing insert 400p'.

Figure 23:
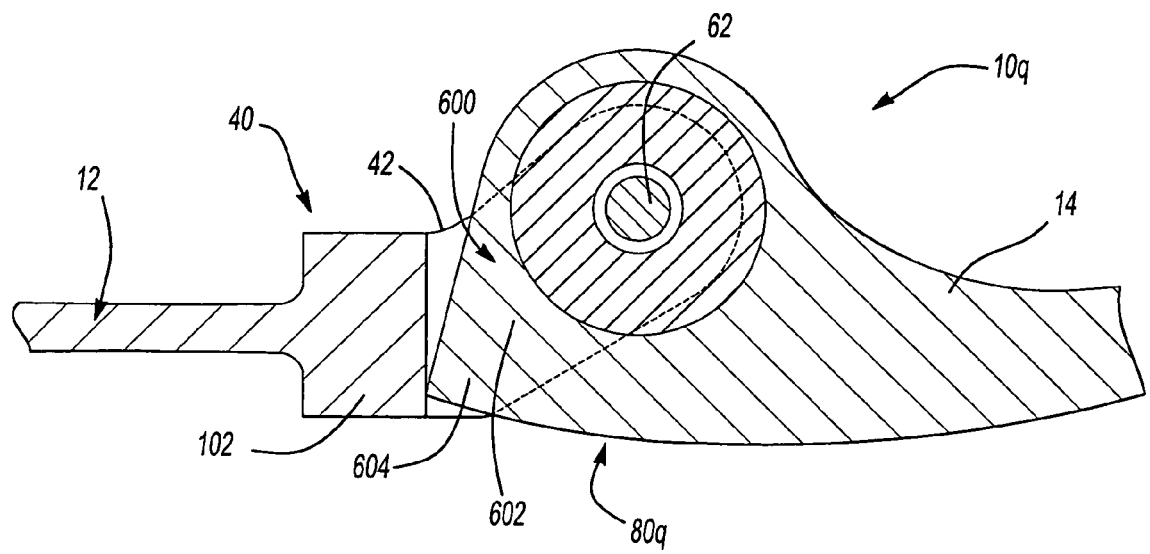
FIG. 23 is a longitudinal cross-sectional view of a linked prosthetic joint kit constructed in accordance with the teachings of a various embodiment of a fourth aspect of the present teachings.
Figure 24:
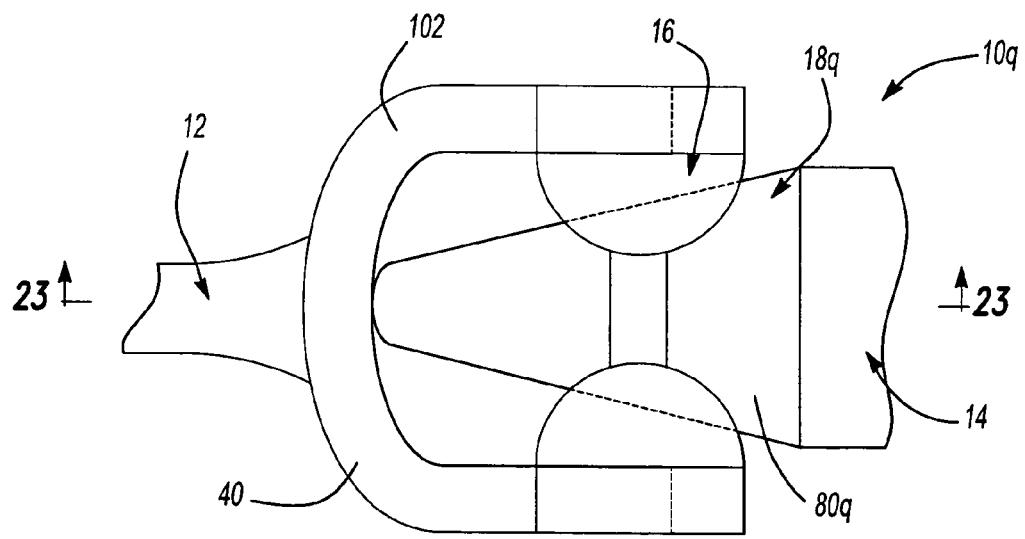
FIG. 24 is a top plan view of the linked prosthetic joint kit of FIG. 23.

In FIGS. 23 and 24, a portion of a modular prosthetic joint kit constructed in accordance with the teachings of a fourth aspect of the present teachings is generally indicated by reference numeral 10q. Prosthetic joint kit 10q is shown to include first stem structure 12, second stem structure 14, first bearing component 16 and second bearing component 18q. Second bearing component 18q is substantially similar to second bearing component 18 except that cage portion 80q is shown to include a cam structure 600. Cam structure 600 includes a lobe member 602 that extends radially outwardly and terminates at a tip 604. Lobe member 602 is configured such that tip 604 contacts the base 102 of U-shaped member 40 to inhibit further relative rotation between first and second stem structures 12 and 14 when the first and second stem structures 12 and 14 are placed in a position corresponding to the maximum extension of a patient's arm. Configuration of second bearing component 18q in this manner is advantageous in that it limits the amount by which a patient may rotate their ulna relative to their humerus to prevent hyperextension of the joint.

In FIGS. 25 and 26, a portion of a modular prosthetic joint kit constructed in accordance with the teachings of a fifth aspect of the present teachings is generally indicated by reference numeral 700. Prosthetic joint kit 700 is shown to include a first stem structure 702 and a second stem structure 704. First stem structure 702 includes a stem member 710, the distal end of which is configured to fit within the medullary canal of an ulna. A first bearing 712 and a coupling structure 714 are incorporated into the proximal end of first stem structure 702. First bearing structure 712 is generally spherically shaped. Coupling structure 714 includes a link member 720 and a retainer member 722. Link member 720 is fixedly coupled to first bearing 712 at a first end and to retaining structure 722 at a second end with link member 720 extending therebetween along an axis generally coincident the longitudinal axis of first stem structure 702. Retaining structure 722 is illustrated to be spherically shaped with flattened ends.

Second stem structure 704 is shown to include a stem member 730 with a proximal end that is configured to fit within the medullary canal of a humerus. A second bearing structure 732 is incorporated into the distal end of second stem structure 704. Second bearing structure 732 includes a generally spherical second bearing surface 740 and a T-shaped coupling aperture 742. A first portion 744 of coupling aperture 742 has a width which is larger than the width of retaining structure 722. First portion 744 is oriented at a position of maximum flexion. In the particular embodiment illustrated, the position of maximum flexion is illustrated to be about 90° to the longitudinal axis of second stem structure 704. However, those skilled in the art will understand that the position of maximum flexion may be tailored in a desired manner and may range as high to an angle of approximately 135° to 150° to the longitudinal axis of second stem structure 704, depending on the particular application. A second portion 746 of coupling aperture 742 has a width which is slightly larger than that of link member 720. Second portion 746 extends circumferentially around a portion of second bearing surface 740 in a plane that coincides with the longitudinal axis of second stem structure 704. The first and second portions 744 and 746 of coupling aperture 742 intersect and terminate at spherically shaped cavity 750.

To use prosthetic joint kit 700, first and second stem structures 702 and 704 are inserted into the medullary canals of the ulna and humerus, respectively. First stem structure 702 is then positioned proximate the first portion 744 of coupling aperture 742 and retaining structure 722 is inserted through first portion 744 and into spherically shaped cavity 750. At this point, first and second bearing surfaces 712 and 740 are in contact with one another and transmit load therebetween rather than through coupling structure 714. Coupling of first and second stem structures 702 and 704 is complete when first stem structure 702 is rotated into second portion 746. In this position, first and second stem structures 702 and 704 are linked or constrained since the width of retaining portion 722 is larger than the width of second portion 746 and thereby prevents the withdrawal of first stem structure 702 from coupling aperture 742.

While the prosthetic joint devices 10 and 10a have been illustrated as having modular flanges 20 that are fixedly but removably coupled to the first stem structure 12, those skilled in the art will understand that the teachings, in its broader aspects, may be constructed somewhat differently. For example, the stem structure and modular flange may be unitarily formed as shown in FIG. 27. In this embodiment, the stem 12p is illustrated to be similar to the stem 12, but includes a flange structure 92p having a flange member 96p and a coupling portion 96p' that couples the flange member 96p to the distal portion 32p of the stem 12p. The flange member 96p is generally parallel the stem member 30p and is employed to compress a bone graft against the stem member 30p. Unlike the modular flange 20 that was described in detail, above, the flange structure 92p must be fitted over a bone graft 110 or the bone graft must be placed into the aperture 800 between the stem member 30p.

Figure 28:
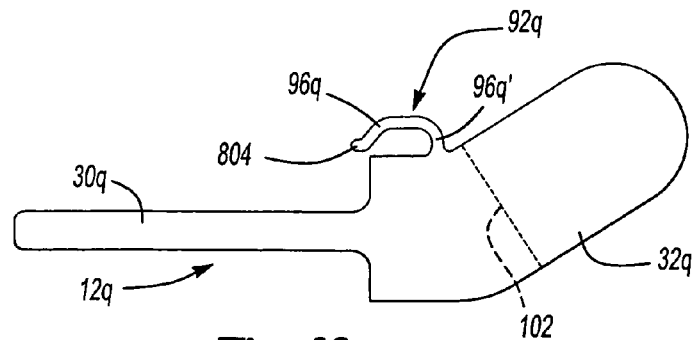
FIG. 28 is a side view illustrating a stem with an integrally-formed, resilient flange for compressing a bone graft.
Figure 29:
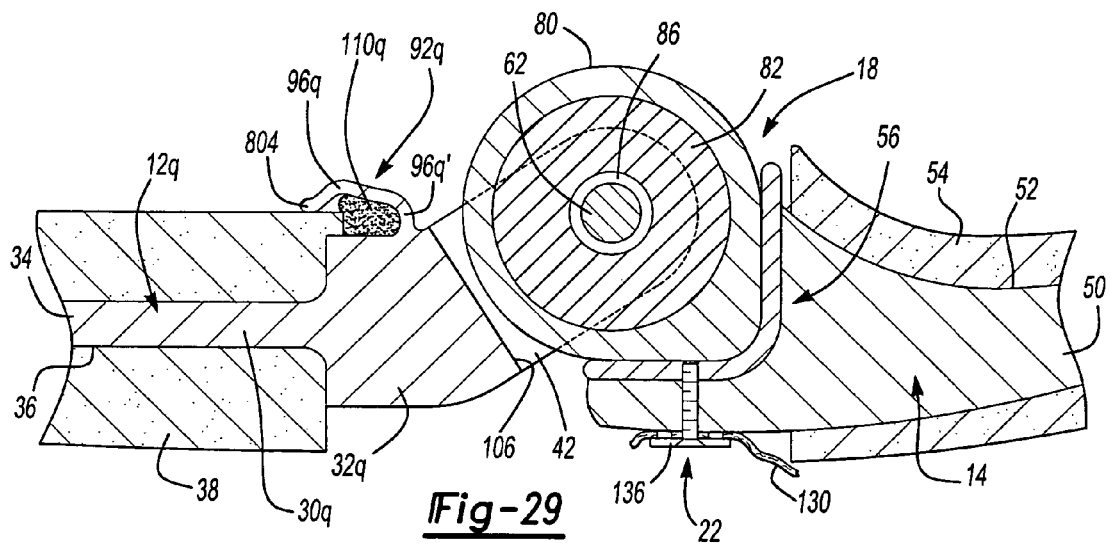
FIG. 29 is a longitudinal cross-sectional view similar to that of FIG. 2, but illustrating the stem of FIG. 28.
Figure 30:
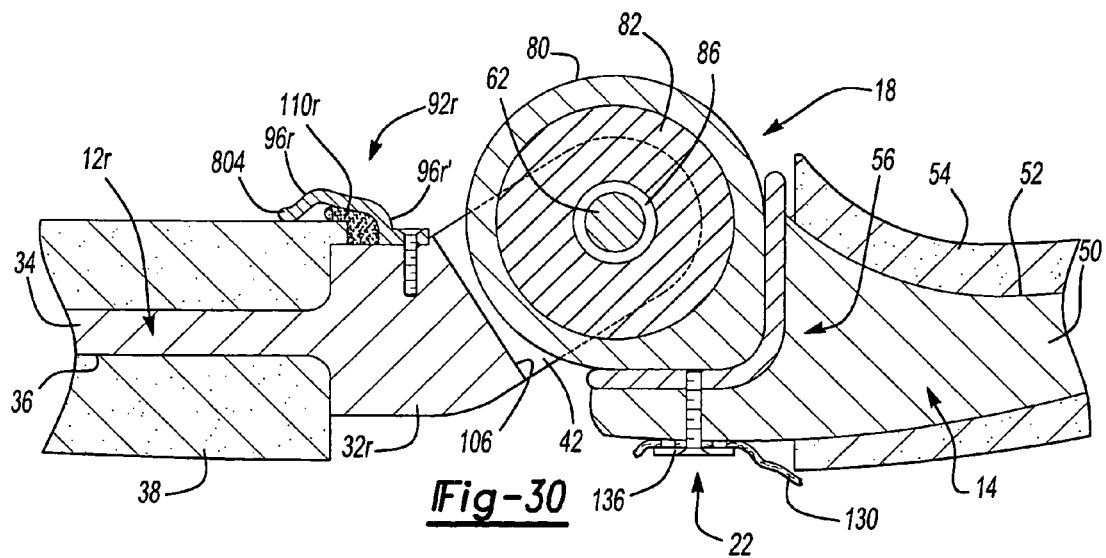
FIG. 30 is a longitudinal cross-sectional view similar to that of FIG. 29, but illustrating the resilient flange as being fixedly but removably coupled to the stem.

Another example of an integrally formed (i.e., non-removable) flange structure is illustrated in FIGS. 28 and 29. In this example, the stem 12q is illustrated to be similar to the stem 12p in that it includes a flange structure 92q having a flange member 96q and a coupling portion 96q' that couples the flange member 96q to the distal portion 32q of the stem 12q. The flange member 96q, however, is arcuately shaped and includes a contact tab 804. The flange structure 92q is formed with a predetermined degree of resiliency, which may result from the characteristics of the material from which the flange structure 92q is formed or by controlling the geometry (i.e., cross-sectional shape and area) of the flange structure 92q. The resiliency of the flange structure 92q permits the flange member 96q to act as a leaf spring that biases the contact tab 804 toward the stem member 30q. Accordingly, the flange may be employed to apply compression to the bone graft 110q without fasteners or other securing means. As illustrated in FIG. 30, those skilled in the art will readily understand, however, that a predetermined amount of resiliency may also be incorporated into a flange structure 92r that is fixedly but removably coupled to the stem 12r.

Figure 31:
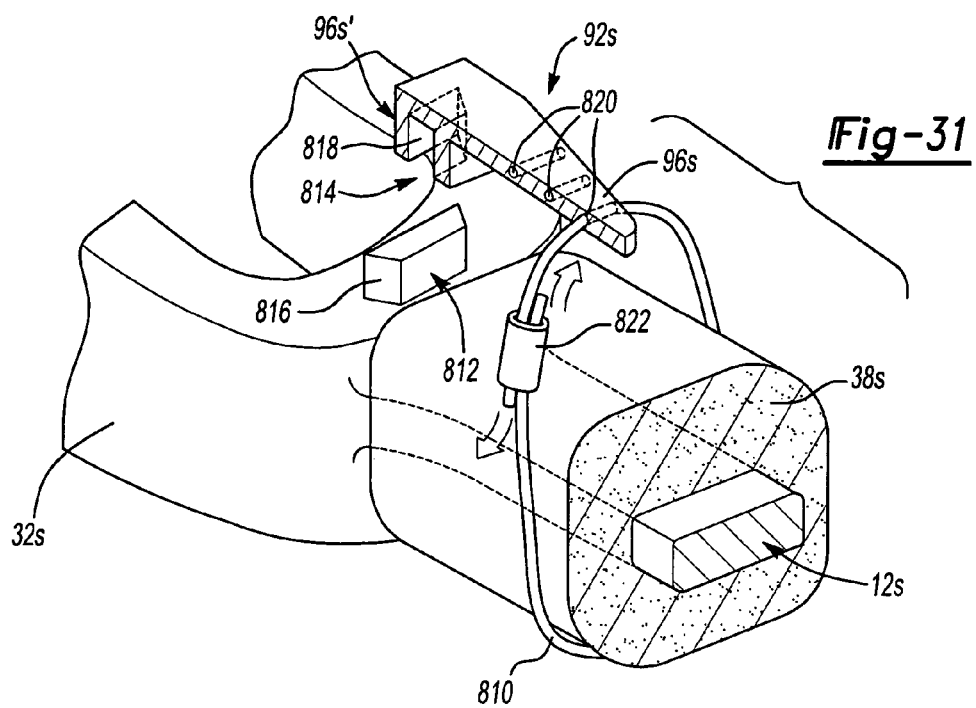
FIG. 31 is a partially broken-away exploded perspective view illustrating an alternative coupling means for coupling the modular flange to the stem.
Figure 32:
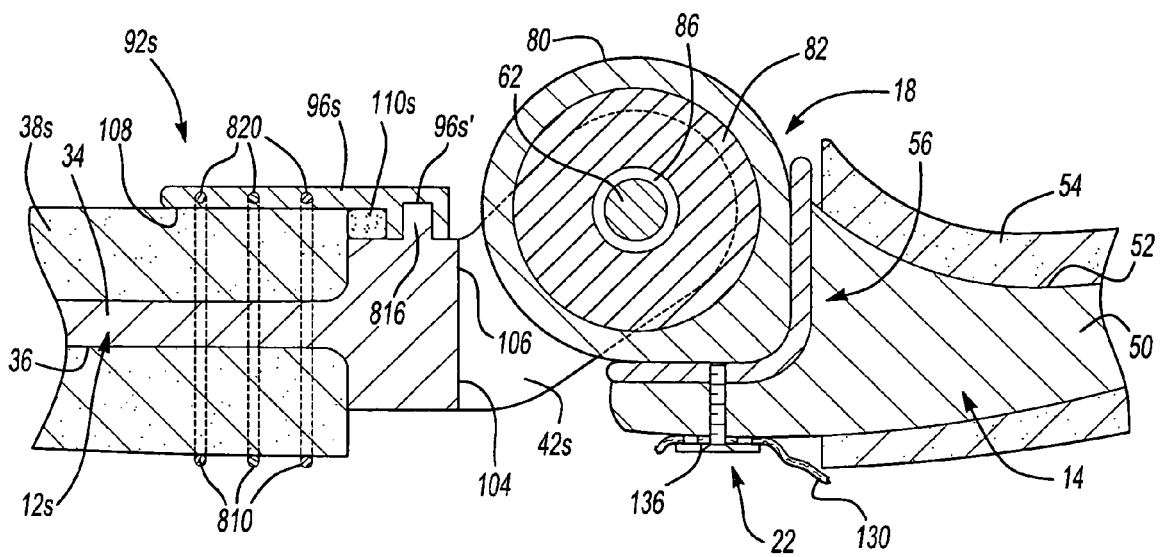
FIG. 32 is a longitudinal cross-sectional view similar to that of FIG. 2, but illustrating the alternative coupling means of FIG. 31.

Those skilled in the art will also understand that although the modular flange 20 has been illustrated as being coupled to the stem 12r via a threaded fastener 94b, the teachings, in its broader aspects, may be constructed somewhat differently. For example, cables 810 are employed to fixedly but removably retain the flange structure 92s to the stem 12s as illustrated in FIGS. 31 and 32. The stem 12s is generally similar to the stem 12, but includes a first coupling feature 812 instead of the bore 100. The flange structure 92s includes a flange member 96s and a coupling portion 96s'. The coupling portion 96s' includes a second coupling feature 814 that is configured to cooperate with the first coupling feature 812 to locate the flange member 96s relative to the distal portion 32s of the stem 12s. In the example illustrated, the first coupling feature 812 is a generally trapezoidal dovetail member 816 that extends outwardly from the distal portion 32s of the stem 12s and the second coupling feature 814 is a dovetail aperture 818 that is formed into the coupling portion 96s' and sized to engage the dovetail member 816 in with a line-to-line fit (i.e., with very little or no clearance). The dovetail member 816 is preferably integrally formed onto the stem 12s but may alternatively be an independently formed component that is fixedly coupled to the distal portion 32s via an appropriate coupling means, such as threaded fasteners, press-fitting or shrink fitting.

The flange member 96s is shown to include a plurality of cross-holes 820 that extend completely through the flange member 96s in a direction that is generally perpendicular the longitudinal axis of the flange member 96s. The cross-holes 820 are sized to receive the cable 810. As those skilled in the art will understand, the cables 810 are first secured around the humerus 38s and the ends of the cables 810 are loosely secured via an appropriate coupling device, such as a cable sleeve 822. The cables 810 are then tensioned to urge the flange member 96s against the humerus 38s and compress the bone graft 110s by a predetermined amount. Thereafter, the coupling device is employed to fix the ends of the cables relative to one another so as to maintain tension in the cables 810.

Figure 33:
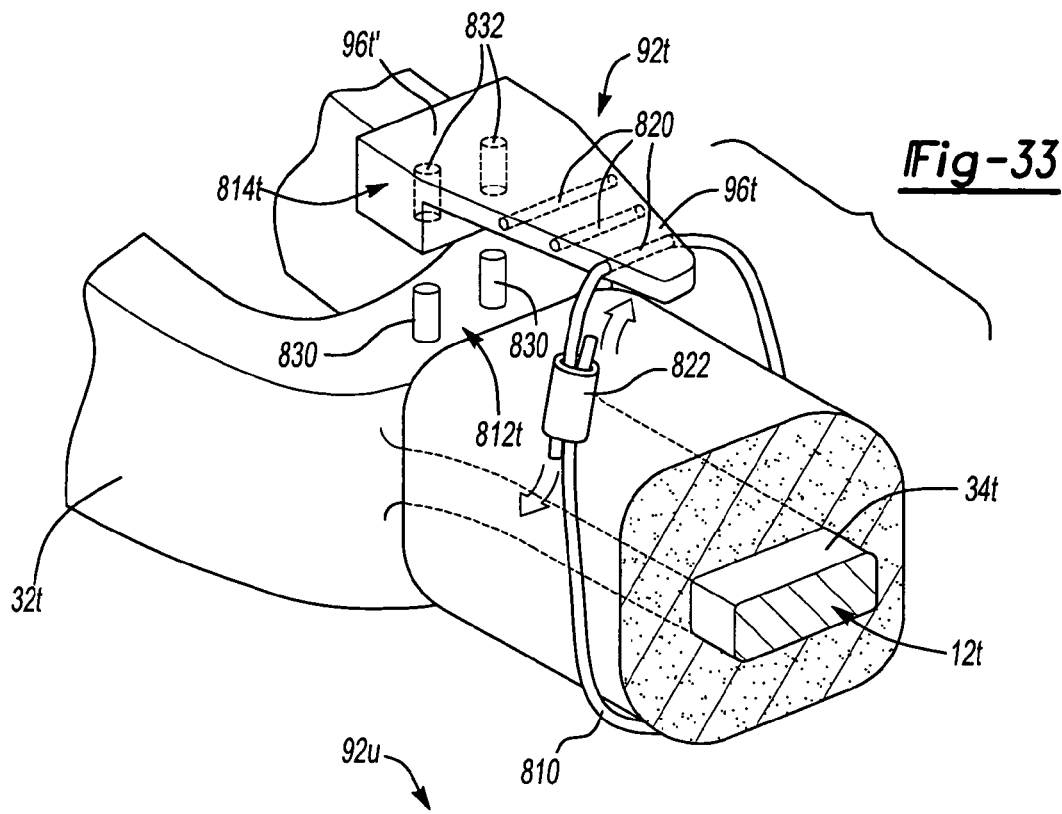
FIG. 33 is a view similar to that of FIG. 31 but illustrating a second alternative coupling means.

While the first and second coupling features 812 and 814 have been illustrated as being a dovetail member 816 and a dovetail aperture 818, respectively, those skilled in the art will appreciate that the first and second coupling features 812 and 814 can be constructed somewhat differently. As illustrated in FIG. 33, for example, the first coupling feature 812t is illustrated as being a pair of pins 830 that are fixedly coupled to the distal portion 32t of the stem 12t and the second coupling feature 814t is illustrated to be a corresponding pair of holes 832 that are formed into the coupling portion 96t. The pins 830 are preferably press-fit or shrunk fit into corresponding holes (not specifically shown) that are formed into the distal portion 32t of the stem 12t but may be secured via other fastening means, such as welding, bonding, or threaded engagement where the pins 830 have a threaded portion that is threadably engaged to the holes in the distal portion 32t. Alternatively, the pins 830 may also be integrally formed as a part of the stem 12t.

Figure 34:
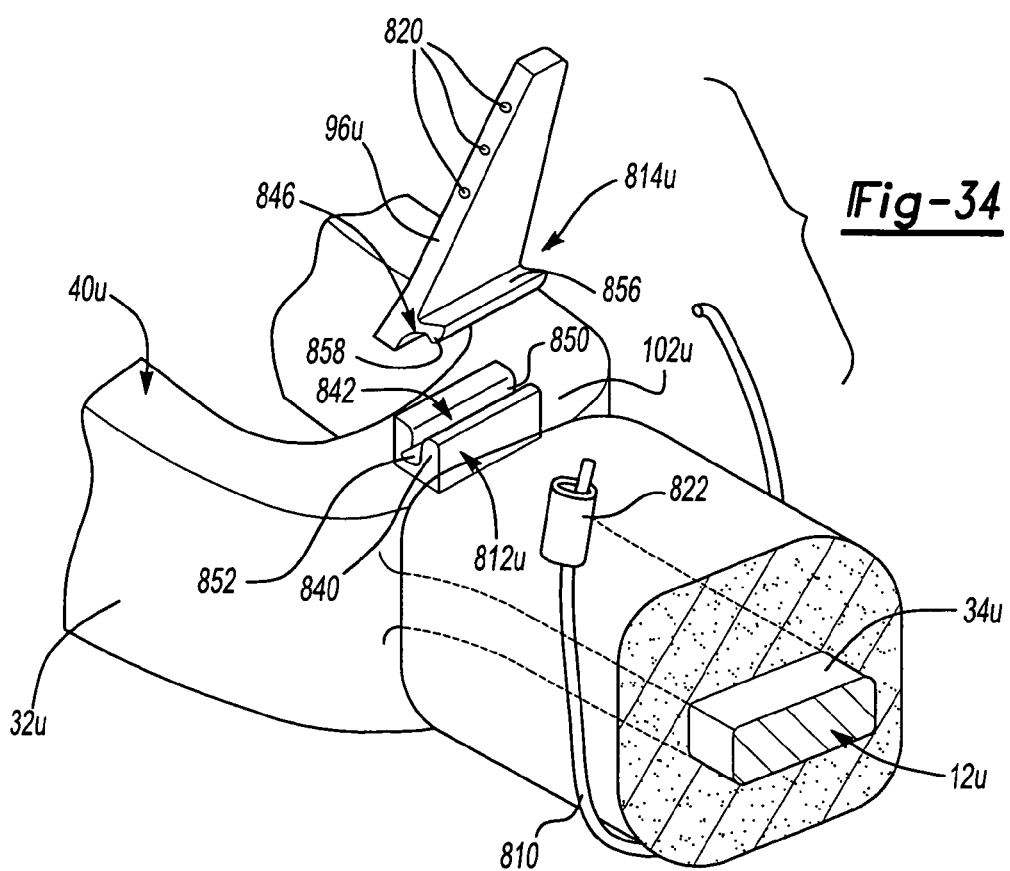
FIG. 34 is a view similar to that of FIG. 31 but illustrating a third alternative coupling means.
Figure 35:
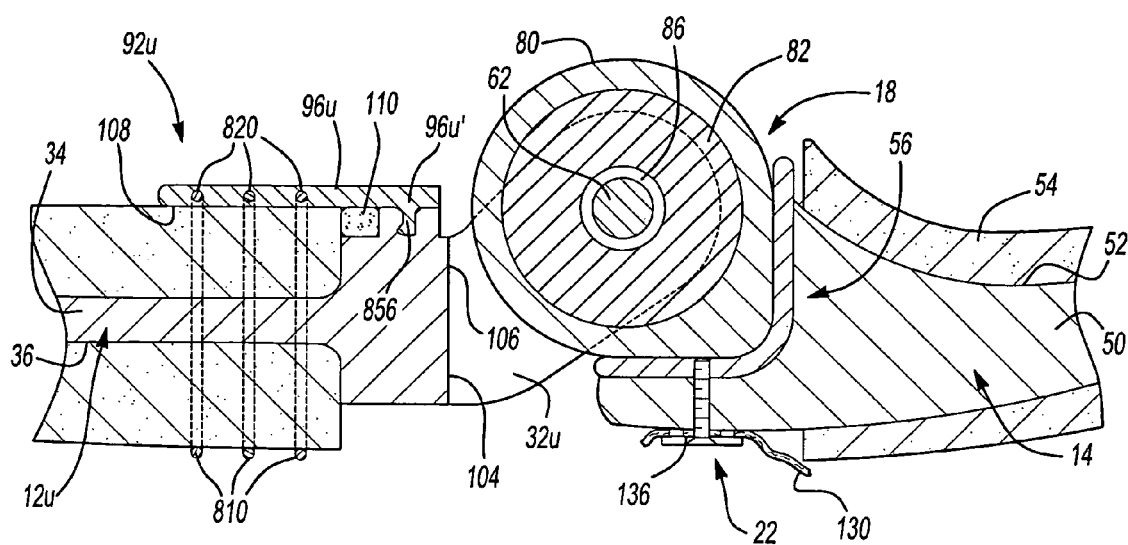
FIG. 35 is a longitudinal cross-sectional view similar to that of FIG. 2, but illustrating the alternative coupling means of FIG. 34.

Another example is illustrated in FIGS. 34 and 35, where the first coupling feature 812u is shown to include a mounting structure 840 with an arcuate mounting aperture 842 and the second coupling feature 814u is shown to include an attachment hook 846. The mounting structure 840 is coupled to the distal portion 32u of the stem 12u and extends generally perpendicularly outwardly from the base 102u of the U-shaped portion 40u. The mounting aperture 842 is generally J-shaped and includes a first portion 850, which is aligned generally perpendicular to the base 102u, and an arcuate second portion 852, which extends away from the stem member 34u and the base 102u. The attachment hook 846 is also generally J-shaped, being configured to matingly engage the mounting aperture 842. In this regard, the attachment hook 846 includes a leg portion 856 that extends downwardly from the flange member 96u and an arcuate base member 858.

In coupling the first and second coupling features 812u and 814u, flange structure 92u is initially positioned relative to the stem 12u such that the base member 858 is disposed within the first portion 850 of the mounting aperture 842. The flange structure 92u is then rotated downwardly toward the stem member 34u to permit the base member 858 to engage the second portion 852 of the mounting aperture 842. The cables 810 are thereafter employed to fix the flange structure 92u relative to the stem 12u.

Figure 36:
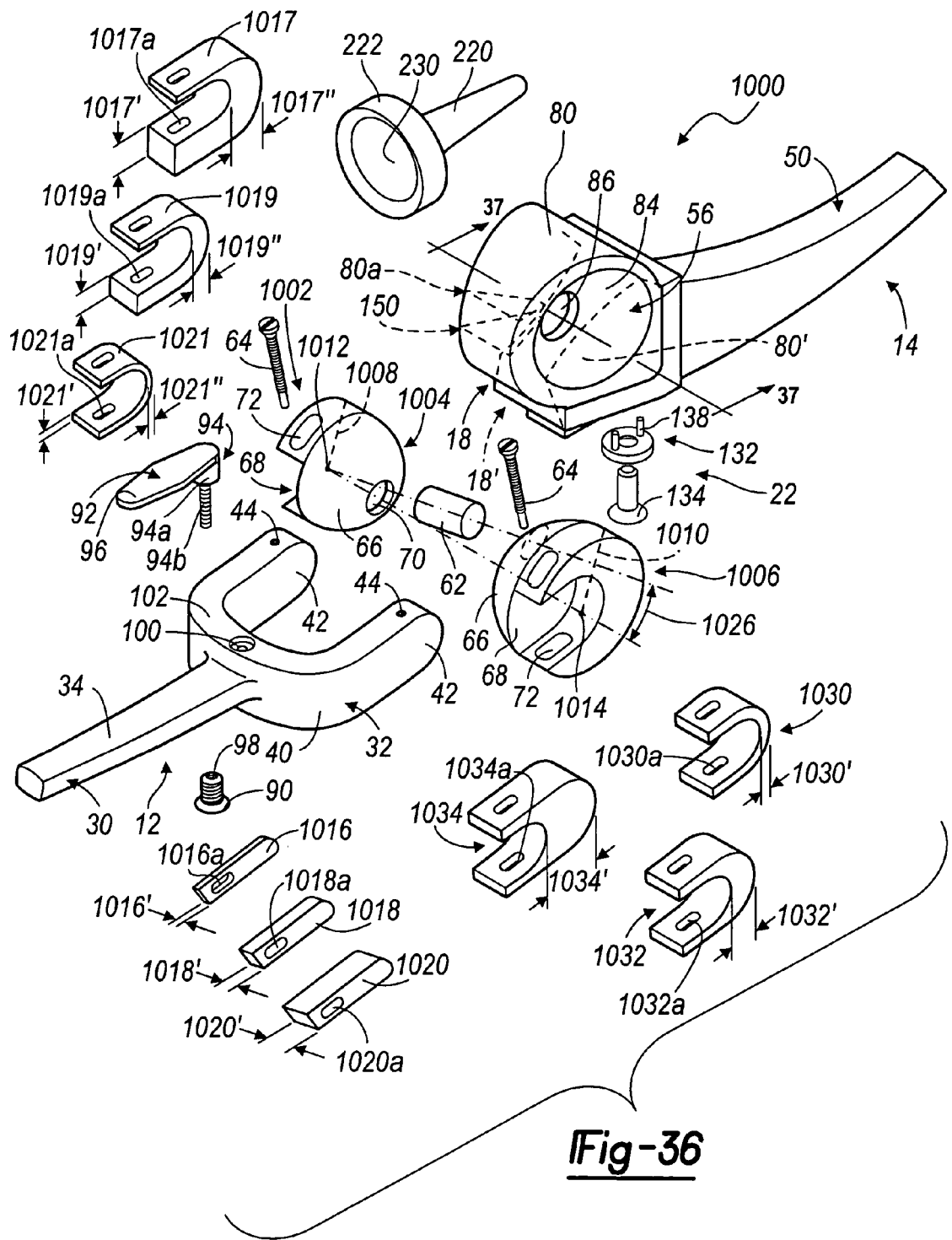
FIG. 36 is an exploded perspective view of a prosthesis according to various embodiments.

With initial reference to FIG. 1 and further reference to FIG. 36, a modular joint prosthesis 1000 is illustrated. It will be understood that the illustrated modular prosthesis 1000 illustrated in FIG. 36 can be similar to the prosthesis 10 illustrated in FIG. 1, though differences can be provided and discussed herein. Nevertheless, like features and portions will be indicated with like reference numerals and not described again in detail. Briefly, however, as discussed above, the modular prosthesis 1000 can be used as a linked elbow prosthesis, although it will be understood according to various embodiments that an unlinked or free elbow prosthesis can be provided, as discussed herein. The prosthesis 1000 can generally include the first stem structure 12, the second stem structure 14, a first bearing component 1002, the second bearing component 18, and various other portions that can be provided or included in the modular prosthesis 1000 if selected. It will be understood that all or various portions are discussed above as included in various embodiments. However, not each of the portions are necessarily provided for each of the embodiments if so selected.

The first bearing component 1002 can define a first condyle portion 1004 and a second condyle portion 1006. The condyle portions 1004, 1006, can be similar to the condyle portions 60 illustrated and described above. According to various embodiments, each of the condyle portions 60 can include substantially similar spherical radii. Although the condyle portion 60 need not define a complete sphere, a portion of the sphere, which they can define, can include or define a spherical radius. According to various embodiments, however, the first condylar portion 1004 can have a first spherical radius 1008 while the second condylar portion 1006 can include a second spherical radius 1010. The first spherical radius 1008 can be different than the second spherical radius 1010.

The spherical radii can be any appropriate dimension such as 1 mm to about 3 cm, such as about 0.6 cm to about 2.0 cm. It will be understood, however, that the spherical radii 1008, 1010, can be any appropriate dimension. For example, the spherical radii 1008, 1010 can be selected for various purposes, such as to substantially mimic a specific anatomy, and as such the various ranges described herein are merely exemplary. Further, it will be understood that the dimensions 1008, 1010, which can include spherical radii, can be any appropriate dimensions. For example, it will be understood that the condylar portions 1004, 1006 need not specifically define a portion of the sphere, a portion of a cylinder, or the like. The condylar portions 1004, 1006 can be irregular such that they are not a regular shape or surface. The design of the condylar portions 1004, 1006 can be specific to various individuals and anatomies, thus not requiring a regular shape.

The condylar portions 1004, 1006 can include the various portions as discussed above. For example, the condylar portions 1004, 1006 can define the bearing portion 66 which can be regular or irregular, as discussed above. Further, each can define the slotted apertures 68 or other appropriate connection portions, to interconnect with the distal portion 32, such as the legs 42 of the first end portion 12. It will be understood that the U-shaped portion 40, which includes the spaced apart the legs 42, can also be referred to as a yoke or other appropriate portion. Further, each of the condyle portions 1004, 1006 can define the pin aperture 70 to interconnect with the condylar pin portion 62 to interconnect the condylar portions 1004, 1006 in a selected manner. As discussed above, however, the condylar portions 1004, 1006, can be substantially formed as a single member or portion that can include the condylar pin 62a as a single portion with the condylar portions 1004, 1006.

Further, as discussed above, the condylar portions 1004, 1006, the condylar pins 62, and any other portions of the prosthesis 1000 can be formed of various materials. For example, it can be selected to form the condylar portions 1004, 1006 from a single material, a composite material, or the like. For example, the condylar portions 1004, 1006 can define the bearing surfaces 66 formed of a polymer material, such as a high molecular weight polyethylene. The second bearing member 18 can also be made of similar materials. Nevertheless, they can also be formed with a metal, metal alloy, ceramic, or the like to achieve various results.

Further, it will be understood that the second bearing portion 18 can include various features and be formed of various materials, including those discussed above. The second bearing member 18 can include the bearing cage 80, the second bearing cage 80a which defines the slot 150, or the substantially unconstrained or unlinked various embodiments that include the bearing member 82' and the features thereof as discussed above. Therefore, it will be understood that the condylar portions 1004, 1006 can be interconnected with any appropriate second bearing portion 18, 18' including those described above.

Further, the prosthesis assembly 1000 can include various portions that allow for the substantial non-linear alignment of the condylar portions 1004, 1006 relative to one another. It can be selected to non-align or offset a first center 1012 of the first condylar portion 1004 and a second center 1014 of the second condylar portion 1006. It will be understood that the centers 1012, 1014, can be any operative center or portion of the prosthesis according to various embodiments and defining a geometrical center is merely exemplary. The centers can be offset in various manners such as an anterior-posterior non-alignment, a superior-inferior non-alignment, or combinations thereof.

For example, an anterior-posterior spacer kit can include a first spacer 1016, a second spacer 1018, and a third spacer 1020. Each of the spacers 1016-1020 can include a dimension 1016'-1020' respectively. The dimensions 1016'-1020' can move or displace the selected condylar portions 1004, 1006 relative to the other. A selected spacer, such as the spacer 1016, can be positioned in the slot 68 such that a passage 1022 through the spacer 1016 aligns with the passage 72 through the condylar portion 1006 so that when the leg 42 is positioned within the slot 68, the leg 42 is unaligned with the first condylar portion 1004. A substantially aligned axis 1024 can pass through the two centers 1012, 1014 of the respective condylar portions 1004, 1006 and through the condylar pin 62. Nevertheless, the spacer 1016 can offset a selected condylar portion, such as the second condylar portion 1006 relative to the first condylar portion 1004. Therefore, an offset angle 1026 can be formed between the first condylar portion 1004 and the second condylar portion 1006.

In various configurations, such as an unaligned configuration, various portions are optional. For example, the pin 62 is optional in various configurations. As discussed above, the bearing members 1002 and 1006 bear the force and the pin can assist with strength and stability of the assembly. Thus is the pin 62 can be omitted between the condyles.

The offset angle or distance 1026 can be any appropriate dimension. The appropriate dimension can be selected for various purposes, such as the specific anatomy of the patient, a selected result, or the like. For example, the offset angle can be about 1° to about 20°, such as about 3° to about 10°. Nevertheless, the offset angle can be any appropriate angle depending upon a selected condition. The offset angle 1026 can be altered by choosing a different one of the spacers 1016-1020 and can be selected pre-operatively, intra-operatively, or at any appropriate time.

Each of the spacers 1016-1020 can include a passage or opening 1016a-1020a. The opening can be a round bore, elongated, a slot or any appropriate opening. The openings 1016a-1020a can be provided to align or be oriented with the openings 72 in the first and second bearing members 1002 or 1006 and a selected passage 1016a-1020a.

The openings 72 can also be circular, oblong, slotted, or formed in any appropriate shape or manner. The interaction of the opening 72 in the bearing members 1002 and 1006 and with the openings 1016a-1020a in the spacers 1016-1020 can help ensure an appropriate fit of the prosthesis 1000.

A second set of spacers 1030-1034 can also be provided. The spacers 1030-1034 can each include a dimension 1030'-1034' respectively. The respective dimension 1030'-1032' can be any appropriate dimension and allow for a selected superior inferior offset. A selected spacer, such as the spacer 1030, can be positioned in the slot 68 to offset the second condylar portion 1006 relative to the first condylar portion 1004. The offset amount can be similar to the angle 1026 except in a different dimension or orientation. The spaces 1030-1034 can also include passages 1030a-1034a, respectively, that can be similar to the passages 1016a-1020a. The passages 1030a-1034a can be round, slotted, oblong, etc. They can be provided to allow for a selected orientation of the prosthesis 1000.

It will be understood, however, that any appropriate number of the various spacers such as the spacers 1016-1020 and the spacers 1030-1034 can be provided for any appropriate purpose. For example, a plurality of the spacers 1016-1020 and 1030-1034 can be provided in minute and discreet differences to allow for an intra-operative selection of a selected offset or to allow for a plurality of offsets for creation from a set of instruments and portions.

With continuing reference to FIG. 36, a third set of spacers 1017, 1019, 1021 can be provided. Although the discussion herein includes a discussion related to three sets of spacers, it will be understood that a set of spacers can include any of the appropriate spacers, all of the spacers, or a selected portion thereof depending upon selected purposes. Nevertheless, the third set of spacers, called that for simplicity of the present discussion, can be formed dissimilar to the second set of spacers 1030-1034. Nevertheless, the third set of spacers 1017-1021 can include a first side 1017a-1021a that has a dimension that is the same or different than a second side 1017b-1021b. The various sides can include any appropriate dimension, however, the dimension of side 1017b-1021b can be varied for various purposes, such as a reason similar to varying the dimension of the first spacer sets 1016-1020. The side 1017b-1021b can include a dimension 1017'-1021' that can be selected for any appropriate purpose, such as a selected offset, including an anterior or posterior offset. The offsets can be any appropriate offsets, and can be similar to, different, or complementary to the offsets of the spacers 1016-1020. Further, the third set of spacers 1017-1021 can include a third side 1017c-1021c. It will be understood that the various sides can be any appropriate portions of the spacers 1017-1021 and has described the sides merely for the discussion herein. Nevertheless, the third side, 1017c-1021c can also include a variable dimension 1017"-1021". The dimension 1017"-1021" can include any appropriate dimension, such as dimensions similar to the dimensions of the second spacer sets 1030-1034.

Therefore the third spacer set 1017-1021 can include a variable dimension of more than one side or portion of the spacers 1017-1021 for various purposes. For example, it can be selected to provide the spacers 1017-1021 to include a selected offset in more than one direction or orientation relative to the prosthesis 1000 or an anatomy into which it is positioned. Therefore, the spacers 1017-1021 can be used to achieve an appropriate orientation of the prosthesis 1000 in a single member. Nevertheless, it will be understood that a modular spacer assembly can be provided to achieve a selected offset in the prosthesis 1000. Having a spacer member that is formed as a single portion or body is not necessary and a modular spacer system can be provided. Nevertheless, a single spacer can include an offset in various dimensions, as exemplary illustrated in the spacers 1017-1021.

Further, the spacers 1017-1021 can include a passage 1017d-1021d similar to the passages described above in the various spacer systems. The passage 1017d-1021d can be circular, oblong, slotted, or any appropriate orientation, size, or the like. The select passage 1017d-1021d can be provided to interact with the passages 72 and the bearing members 1002 and 1006 to achieve a selected orientation of the spacer members relative to the bearing members 1002 1006.

Figure 37:
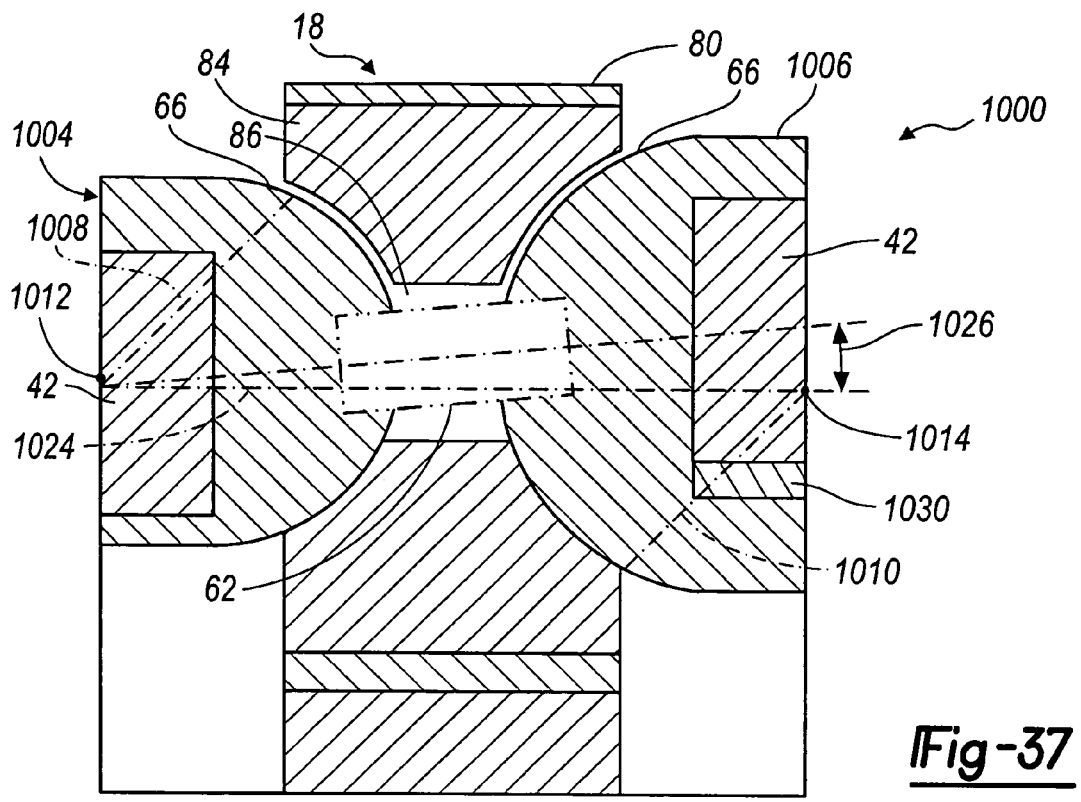
FIG. 37 is a detailed cross-sectional view of an assembled prosthesis according to various embodiments.

With reference to FIG. 37 and continuing reference to FIG. 36, the detailed cross-sectional view of the condylar portions 1004, 1006 relative to the second bearing member 18 is illustrated in an assembled manner. As illustrated in FIG. 37, a selected one of the spacers, such as the spacer 1030 can be inserted into the slot 68 to displace the second condylar portion 1006 relative to the first condylar portion 1004. Therefore, the angle 1026 is formed between the first center 1012 and the second center 1014 with the condylar portions 1004, 1006. Further, as illustrated in FIG. 37, the second condylar portion 1006 can include the dimension 1010 that is larger than the dimension 1008 of the first condylar portion 1004. Thus, the condylar portion 1006 can be designed to mimic a selected portion of the anatomy, if so selected.

Nevertheless, it is still understood that the bearing surfaces 66 can bear on the bearing member 84 of the second bearing member 18 in an appropriate manner. Thus, the condylar pin 62 does not or is not required for proper articulation and may not engage a selected portion of the bearing member 84 after positioning or implantation of the prosthesis 1000. For similar reasons, the pin 62 is not required in the assembly as discussed above. The pin 62 can be omitted for various reasons, such as ease of assembly. Although one skilled in the art will understand that the pin 62 can be used for various reasons, including stability, strength, alignment, and the like. Also, the selected anatomical geometry can be obtained with the prosthesis 1000, which can use any or a plurality of the spacers 1016-1020, 1030-1034, or 1017-1021 to achieve any appropriate offset or angle and also the dimension of the condylar portions 1004, 1006 can be selected to achieve the appropriate results.

Figure 38:
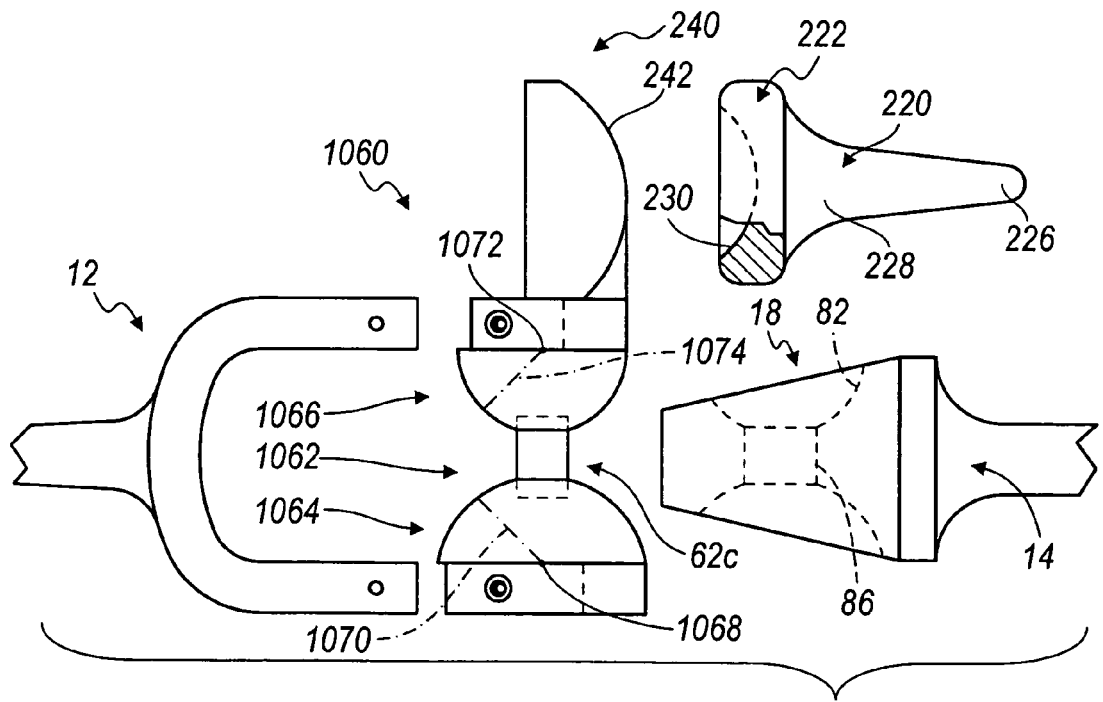
FIG. 38 is an exploded plan view of a prosthesis according to various embodiments.

With reference to FIG. 38, a modular prosthesis assembly 1060 can include various portions, including those discussed above. It will be understood that the similar portions can be referenced by like numerals and a detailed description thereof need not be necessary here to understand the various embodiments. Nevertheless, the first stem assembly 12 can be provided to interconnect with a first bearing assembly 1062 and a second stem assembly 14 and a third stem assembly 220. As discussed above, the fourth bearing component 222 can be provided with the stem assembly 220 to interconnect with the radius to replace articulating portion thereof. It will be understood that the stem assembly 220 can be provided with various portions to achieve a replacement of a selected portion of the radius.

It will be further understood that, as described above in various embodiments, that the bearing portion 222 can be formed as a single member with the second stem assembly 14 according to various embodiments. The first bearing assembly 1062 can include a first condylar portion 1064, a second condylar portion 1066 and the extension 240. The extension 240 can be provided to extend from a selected portion of the first bearing member 1062 such as medial or laterally from the first bearing member 1062. The extension 240 can define the extension bearing member 242 that can articulate with the bearing portion 222 of the stem 220 or with the natural portion of the radius. Further, as discussed above, the bearing surface 222 can articulate with the natural portion of the humerus if so selected. Also, the second bearing member 18 can be provided in a substantially linked, unlinked or unconstrained, semi-constrained or linked, or a slot that allows access to the bore 86 in any appropriate manner.

The first bearing member 1062 can be interconnected with the first stem member 12 in any appropriate manner, including the various screws or fixing member 64 as described above. Further, the condylar portions 1064, 1066 can be interconnected with the condylar pin 62c in any appropriate manner, including those discussed above. Nevertheless, the first condylar member 1064 can be provided in a different manner, geometry, size, etc., than a second condylar member 1066.

As discussed above, the first condylar member 1064 can have a centerpoint 1068 that can define a center of a sphere or any other regular or irregular shape. For example, the first condylar portion 1064 can define a spherical radius 1070 that extends from the center 1068 to an edge of the condylar member 1064. The second condylar member 1066 can also define a center 1072, which can be the center of a sphere or any other appropriate shape or irregular shape. Further, the second condylar portion can define a second spherical radius 1074. As discussed above, the spherical radii 1070, 1074 can be provided to be equal, different, or in any appropriate combination. Nevertheless, it will be understood that the condylar portions 1064, 1066 can include a different dimension and be interconnected with the various portions, such as the extension 242 to articulate with various portions of the anatomy or prostheses positioned therein. It will also be understood that the condylar portions 1064, 1066 can interconnect with the first stem member 12 in any appropriate manner. Therefore, various further portions, such as the spacers 1016-1020, 1030-1034, or 1017-2021 can be provided with the prosthesis system 1060.

It will be understood that the various embodiments of the prostheses, whether linked or unlinked or constrained or unconstrained can be provided in various portions of the anatomy. Nevertheless, the exemplary elbow prostheses can be provided in various manners for selection by a user. As discussed above, a kit can include each and every of the various portions of the various embodiments for selection by a user during an operative procedure, prior to an operative procedure, or at any appropriate time. Therefore, the modular prosthesis, according to various embodiments, can be provided for use by a user in a selected manner to achieve a selected result.

Figure 39:
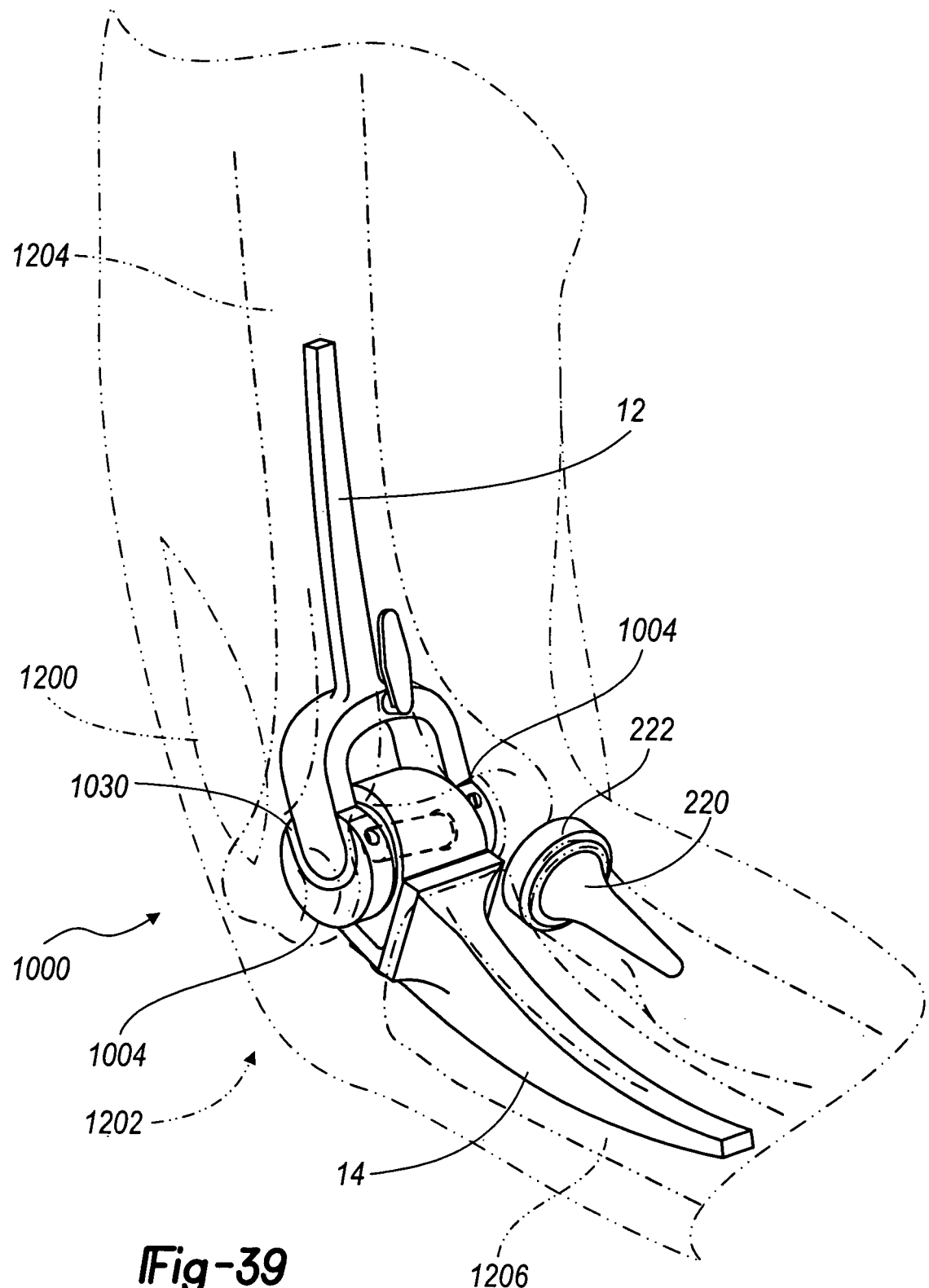
FIG. 39 is a detailed environmental view of a prosthesis implanted in an anatomy according to various embodiments.

Further, with exemplary reference to FIG. 39, the prosthesis 1000 can be positioned in the anatomy in any appropriate manner. The modular prosthesis can be provided to be positioned relative to various portions of the anatomy, such as a humerus, a radius, an ulna, or any appropriate portions through a selected incision 1200 relative to the elbow 1202 joint between the hummers 1204 and ulna 1206. It will be understood that the modular nature of the prosthesis 1000, can be provided for a procedure that can be performed through a relatively minor incision that need not be larger than various portions of the modular prosthesis. This can achieve various results, such as minimizing recovery time, minimizing operation time, or various selected results. Further, as discussed above, the modular nature of the various portions and various embodiments can provide for achieving a selected revision procedure. For example, having the various sizes of the condylar portions, which can include different dimensions, a revision procedure can be provided to maintain or augment a selected result to achieve a more anatomical result in a selected period. Further, the prosthesis, according to various embodiments, can be changed from a constrained to unconstrained or from an unconstrained to a constrained. The change can be provided during a selected procedure, such as a revision procedure to account for changes in the anatomy over time. Nevertheless, the modular prosthesis according to various embodiments can be provided for selection by a user to achieve a more natural anatomical result after implantation of the prosthesis.

While the description in the specification and illustrated in the drawings are directed to various embodiments, it will be understood that various changes may be made and equivalents may be substituted for elements thereof without departing from the scope of the teachings and the appended claims. In addition, many modifications may be made to adapt a particular situation or material to the teachings without departing from the scope thereof. Therefore, it is intended that the teachings and claims are not be limited to any particular embodiment illustrated in the drawings and described in the specification, but that the teachings and claims can include any embodiments falling within the foregoing description and the appended claims.

What is claimed:

1. A prosthesis assembly for implanting into an anatomy, comprising:
    a first stem member to be positioned in a first portion of the anatomy and including a first longitudinal axis;
    a first condylar bearing member having a first operative center;
    a second condylar bearing member having a second operative center;
    a pin member extending between the first condylar bearing member and the second condylar bearing member and including a second longitudinal axis extending through the first operative center of the first condylar bearing member, through the second operative center of the second condylar bearing member, and substantially perpendicular to the first longitudinal axis in a first orientation;
    a spacer member to be positioned between the first stem member and at least one of the first condylar bearing member, the second condylar bearing member, or combinations thereof to offset the first operative center from the second operative center and position the first longitudinal axis in a second orientation different than the first orientation.

2. The prosthesis assembly of claim 1, wherein the offset includes at least one of an anterior to posterior offset, a superior to inferior offset, or combinations thereof.

3. The prosthesis assembly of claim 1, wherein the first condylar bearing member and the second condylar bearing member both define bearing member slots operable to interconnect with a portion of the first stem.

4. The prosthesis assembly of claim 3, wherein the first stem includes a first leg and a second leg wherein the first leg is operable to interconnect with the bearing member slot fo the first condylar bearing member and the second leg is operable to interconnect with the bearing member slot of the second condylar bearing member.

5. The prosthesis assembly of claim 4, wherein the spacer member is operable to be positioned relative to the bearing member slot of the first condylar bearing member, the second leg in the bearing member slot of the second condylar bearing member, or combinations thereof;
    wherein the spacer selects a position of the leg relative to the respective first condylar bearing member, the second condylar bearing member, or combinations thereof.

6. The prosthesis assembly of claim 1, wherein said spacer member includes a plurality of spacer members, each having a different dimension.

7. The prosthesis assembly of claim 6, wherein the different dimension provides a selected offset of the first condylar bearing member relative to the second condylar bearing member.

8. The prosthesis assembly of claim 1, wherein the spacer is operable to be positioned anteriorly, posteriorly, inferiorly, medially, laterally, or combinations thereof relative to the first stem member.

9. A prosthesis assembly for replacing a selected portion of an anatomy, comprising:
    a first stem member to be positioned in a humerus;
    a first hemispherical bearing member to replace a first portion of the humerus having a first radius of curvature relative to a first operative center of rotation; and
    a plurality of second hemispherical bearing members to replace a second portion of the humerus having a second radius of curvature different than the first radius of curvature relative to a second operative center of rotation; and a plurality of spacer members to position between the first stem member and at least one of the first hemispherical bearing member, at least one of the plurality of second hemispherical bearing members, or combinations thereof to achieve a selected offset between the first operative center of rotation and the second operative center of rotation.

10. The prosthesis assembly of claim 9, further comprising:

a connecting member to interconnect the first hemispherical bearing member and a selected one of the plurality of second hemispherical bearing members.

11. The prosthesis assembly of claim 10, further comprising:

a third bearing member to articulate only with the first hemispherical bearing member, the selected of the plurality of the second hemispherical bearing members, or combinations thereof.

12. The prosthesis assembly of claim 11, wherein the third bearing member extends from a second stem member to be positioned relative to the humerus.

13. The prosthesis assembly of claim 9, wherein the first hemispherical bearing member defines a first slot, each of the plurality of the second hemispherical bearing members define a second slot, wherein the first stem member includes a portion operable to extend into the at least one of the first slot, the second slot, or combinations thereof.

14. The prosthesis assembly of claim 13, wherein at least one of the plurality of spacer members is positioned in at least one of the first slot, the second slot, or combinations thereof.

15. The prosthesis assembly of claim 9, wherein the plurality of spacer members are positioned relative to the first hemispherical bearing member and at least one of the plurality of second hemispherical bearing members to obtain a selected offset that is at least one of an anterior to posterior offset, a superior to inferior offset, a medial to lateral offset, or combinations thereof.

\* \* \* \* \*

UNITED STATES PATENT AND TRADEMARK OFFICE
CERTIFICATE OF CORRECTION

PATENT NO. : 8,585,768 B2
APPLICATION NO. : 11/384943
DATED : November 19, 2013
INVENTOR(S) : Brian K. Berelsman et al.

It is certified that error appears in the above-identified patent and that said Letters Patent is hereby corrected as shown below:

In the Specification
Column 2, Background, Line 12, Delete "a" and insert --an--.
Column 7, Detailed Description Of Various Embodiments, Line 48, Delete "form" and insert --from--.
Column 7, Detailed Description Of Various Embodiments, Line 51, Delete "form" and insert --from--.
Column 13, Detailed Description Of Various Embodiments, Line 55, Delete "form" and insert --from--.

In the Claims
Column 24, Claim 4, Line 37, delete "fo" and insert --of--.
Column 24, Claim 5, Line 42, after "the", insert --first leg in the--.

Signed and Sealed this
Twenty-first Day of October, 2014

Michelle K. Lee
*Deputy Director of the United States Patent and Trademark Office*